US010576165B2

(12) United States Patent
Tyavanagimatt et al.

(10) Patent No.: US 10,576,165 B2
(45) Date of Patent: Mar. 3, 2020

(54) ST-246 LIQUID FORMULATIONS AND METHODS

(71) Applicant: SIGA TECHNOLOGIES, INC., Corvallis, OR (US)

(72) Inventors: Shanthakumar R. Tyavanagimatt, Corvallis, OR (US); Melialani A. C. L. S. Anderson, Corvallis, OR (US); William Weimers, Corvallis, OR (US); Gopi Krishna Kasi, Lynnwood, WA (US); N K Peter Samuel, Corvallis, OR (US); Tove C. Bolken, Keizer, OR (US); Dennis E. Hruby, Albany, OR (US)

(73) Assignee: Siga Technologies Inc., Corvallis, OR (US)

(*) Notice: Subject to any disclaimer, the term of this patent is extended or adjusted under 35 U.S.C. 154(b) by 0 days.

(21) Appl. No.: 16/157,343

(22) Filed: Oct. 11, 2018

(65) Prior Publication Data

US 2019/0038767 A1 Feb. 7, 2019

Related U.S. Application Data

(62) Division of application No. 15/872,505, filed on Jan. 16, 2018, now Pat. No. 10,124,071, which is a division of application No. 14/955,674, filed on Dec. 1, 2015, now Pat. No. 9,907,859, which is a division of application No. 13/814,102, filed as application No. PCT/US2011/046260 on Aug. 2, 2011, now Pat. No. 9,233,097.

(60) Provisional application No. 61/370,971, filed on Aug. 5, 2010, provisional application No. 61/450,359, filed on Mar. 8, 2011.

(51) Int. Cl.
| | |
|---|---|
| *A61K 47/69* | (2017.01) |
| *A61K 31/4035* | (2006.01) |
| *A61K 9/00* | (2006.01) |
| *A61K 47/10* | (2017.01) |
| *A61K 47/40* | (2006.01) |
| *A61K 31/715* | (2006.01) |
| *A61K 31/724* | (2006.01) |
| *A61K 9/08* | (2006.01) |
| *A61K 47/26* | (2006.01) |

(52) U.S. Cl.
CPC ........ *A61K 47/6951* (2017.08); *A61K 9/0014* (2013.01); *A61K 9/0019* (2013.01); *A61K 9/08* (2013.01); *A61K 31/4035* (2013.01); *A61K 31/715* (2013.01); *A61K 31/724* (2013.01); *A61K 47/10* (2013.01); *A61K 47/26* (2013.01); *A61K 47/40* (2013.01); *C12N 2710/24071* (2013.01)

(58) Field of Classification Search
CPC .......................... A61K 31/4035; A61K 31/724
USPC .......................................... 514/416, 417, 58
See application file for complete search history.

(56) References Cited

U.S. PATENT DOCUMENTS

| | | | |
|---|---|---|---|
| 2003/0220294 A1 | 11/2003 | Wallace et al. | |
| 2007/0287735 A1 | 12/2007 | Jordan et al. | |
| 2009/0011037 A1 | 1/2009 | Pipkin et al. | |

FOREIGN PATENT DOCUMENTS

| | | |
|---|---|---|
| JP | 2010-510311 A | 4/2010 |
| WO | WO-2004112718 A2 | 12/2004 |
| WO | WO-2008-130348 A1 | 10/2008 |
| WO | WO-2010-014913 A1 | 2/2010 |

OTHER PUBLICATIONS

Office Action issued in Chinese Counterpart Application No. 201610599807.0, dated Jan. 2, 2019.
Office Action issued in Israel Counterpart Application No. 224430, dated Nov. 14, 2018.
Examination Report issued in Counterpart Mexican Application No. MX/a/2017/006160 dated Feb. 27, 2019 with English language translation thereof.
Examination report issued in European Counterpart Application 11 815 188.5 dated Oct. 2, 2018.
Japanese Office Action from Japanese Application No. 2013-523271, dated Jul. 17, 2015.
Tiwari, G., et al., "Cyclodextrins in delivery systems: Application." Journal of Pharmacy and Bioallied Science, Apr. 2010, vol. 2, No. 2, pp. 72-79.
Thorsteinn, L., "Pharmaceutical Applications of Cyclodextrins. 1. Drug Solubilization and Stabilization," Journal of Pharmaceutical Sciences, Oct. 1996, vol. 85, No. 10, pp. 1017-10-25.
Australian Patent Examination Report No. 1, issued in Australian Patent Application 2011285871, dated Aug. 7, 2013.
Smee, D., et al. "Efficacy of N-methanocarbathymidine in Treating Mice Infected Intranassally with the IH-D and WR strains of vaccine virus." Antiviral Research. 2007, vol. 76, pp. 124-129; Abstract p. 2, para 5.
International Search Report from International Application PCT/US2011/46260, dated Dec. 20, 2011.
European Search Report issued in European Application No. 1181588.5 dated Mar. 22, 2016.
Rajewski, Roget et al. "Pharmaceutical Applications of Cyclodextrins 2 In Vivo Drug Delivery" Journal of Pharmaceutical Sciences, American Pharmaceutical Assocation1996. vol. 85, No. 1, pp. 1142-1169.

(Continued)

*Primary Examiner* — Kevin E Weddington
(74) *Attorney, Agent, or Firm* — Charles C. Achkar; Ostrolenk Faber LLP.

(57) ABSTRACT

The present invention provides for a novel liquid formulation for solubilizing poorly soluble ST-246 in cyclodextrins and a novel process of making the formulation.

8 Claims, 21 Drawing Sheets

(56) References Cited

OTHER PUBLICATIONS

Challa, Rajeswari, et al. "Cyclodextrins in drug delivery: an updated review" AAPS Pharmscitech, Springer New York LLC, US. 2005. vol. 6. No. 2, pp. e329-e357.
Examination Report issued in Indian Counterpart Application 305/KOLNP/2013 dated Nov. 30, 2017.
Office Action issued in Korean Counterpart Application 1020137005710, dated Jan. 29, 2018.
Office Action issued in Chinese Counterpart Application 201610599807.0, dated Apr. 5, 2018.
Lu Bin, "New Dosage Forms and New Techniques of Drugs" ($2^{nd}$ edition), People's Medical Publishing House, $2^{nd}$ edition in 2005-07, pp. 34-35.
Office Action issued in Korean Counterpart application No. 1020137005710 dated Jan. 29, 2018.
Examination Report issued in Counterpart Chinese Application No. 201610599807.0 dated Jun. 18, 2019 with English language translation thereof.
Examination Report issued in Counterpart Argentina Application No. P110102829 dated May 24, 2019 with English language translation thereof.
"Chinese Materia Medica Preparation Technology",IIC 161797—common knowledge evidence (Chang Yiling edited), published Aug. 31, 2009.
"Pharmaceutics" IIC 161797—common knowledge evidence (Chen Qiong edited), published Jun. 30, 2008.

ST-246 LIQUID FORMULATIONS AND METHODS

CROSS REFERENCE TO RELATED APPLICATIONS

The present application is a divisional of U.S. application Ser. No. 15/872,505, filed Jan. 16, 2018, which is a divisional of U.S. application Ser. No. 14/955,674, filed Dec. 1, 2015, now U.S. Pat. No. 9,907,859, which is a divisional of U.S. application Ser. No. 13/814,102, filed Sep. 17, 2013, now U.S. Pat. No. 9,233,097, which is a § 371 National Phase application based on PCT/US2011/046260, filed Aug. 2, 2011, which claims benefit to U.S. Provisional Application No. 61/370,971, filed on Aug. 5, 2010 and U.S. Provisional Application No. 61/450,359, filed Mar. 8, 2011, the subject matter of each of which is incorporated by reference in their entirety.

STATEMENT REGARDING FEDERALLY SPONSORED RESEARCH OR DEVELOPMENT

This invention was made with U.S. government support under Contract No. HHSN272200800041C awarded by the Biomedical Advanced Research and Development Authority and the National Institute of Health (NIH). The U.S. Government has certain rights in the invention.

FIELD OF THE INVENTION

The present invention relates to novel liquid formulations of ST-246 and processes for making the liquid formulation.

BACKGROUND OF THE INVENTION

Throughout this application, various publications are referenced within the text. The disclosure of these publications in their entireties are hereby incorporated by reference into this application in order to more fully describe the state of the art as known to those skilled in therein as of the date of the invention described and claimed herein.

Historically, variola virus, the etiologic agent of smallpox, has been estimated to have killed, crippled, or disfigured nearly 10% of the human population prior to eradication (1). Smallpox is highly communicable and carries exceptionally high morbidity. Secondary attack rates among unvaccinated members of households in which someone had smallpox have been reported to range from 30% to 80%. Mortality rates range from 1% for variola minor to 30% for variola major. With the advent of biowarfare as an instrument of terrorism, smallpox can no longer be thought of as a disease of historic impact only.

There are currently no therapies other than early vaccination that can alter the outcome of disease or potentially prevent disease in a population that has been exposed to smallpox. Vaccination carries an inherent risk of adverse events for certain immunosuppressed recipients and even some healthy recipients (2). Moreover, vaccination is effective only if administered within 4 days post-exposure. Thus, antiviral drugs used alone or potentially in combination with vaccination can be used to treat individuals during the window of vulnerability which occurs prior to development of protective immunity. Additionally, antiviral drugs could also be used in the treatment of zoonotic poxvirus disease in humans, such as monkeypox.

ST-246 (4-trifluoromethyl-N-(3,3a,4,4a,5,5a,6,6a-octahydro-1,3-dioxo-4,6-ethenocycloprop[f]isoindol-2(1H)-yl)-benzamide), has recently emerged as a potent candidate against orthopoxvirus. Several studies evaluating ST-246 for activity against orthopoxviruses have demonstrated excellent in vitro and in vivo efficacy (3, 4). When evaluated in vitro against vaccinia virus (VV), cowpox virus (CV), ectromelia virus (ECTV), monkeypox, camelpox, and variola viruses, ST-246 inhibited virus replication by 50% (50% effective concentration [EC50]) at or below a concentration of 0.07 µM. With animal models using lethal infections with ECTV, VV, or CV, ST-246 was reported to be nontoxic and highly effective in preventing or reducing mortality even when treatments were delayed up to 72 h post-viral inoculation (3, 4). ST-246 was also evaluated with the nonlethal mouse tail lesion model using intravenous VV. When ST-246 was administered orally twice a day at 15 or 50 mg/kg of body weight for 5 days, the tail lesions were significantly reduced (4). Most recently, an infant was given ST-246 as an FDA-authorized emergency treatment for eczema vaccinatum which developed after exposure to the parent's predeployment military smallpox immunization (5).

Given the high efficacy of ST-246 antiviral therapy against smallpox and a lack of FDA-approved medications for the treatment of smallpox infection, there is clearly a need for developing safe and effective ST-246 formulations that can be administered by various routes of administration. However, the poor solubility of ST-246 in water and in pharmaceutically acceptable pH buffers creates an impediment to making safe and effective ST-246 liquid formulations.

Thus, there is a critical need in the pharmaceutical and other biological based industries to formulate water insoluble ST-246 into liquid formulations for oral, parenteral, or topical administration.

SUMMARY OF THE INVENTION

The present invention provides a liquid pharmaceutical formulation comprising a therapeutically effective amount of ST-246 and cyclodextrin, and further comprising one or more pharmaceutically acceptable ingredients.

The present invention also provides methods of treating orthopoxvirus infections and/or eczema vaccinatum comprising administering to a subject in need thereof a liquid pharmaceutical formulation according to the present invention.

The present invention further provides a process of making a liquid formulation according to the present invention comprising the steps of: a) mixing ST-246 with cyclodextrin in a pharmaceutically acceptable liquid carrier; and b) optionally filtering the mixture of step a).

The present invention also provides a unit dosage liquid formulation comprising: a) ST-246 content ranging from about 2 mg/ml to about 20 mg/ml; and b) hydroxypropyl-β-cyclodextrin content ranging from about 12.5 mg/ml to about 40 mg/ml.

The present invention further provides a unit dosage liquid formulation comprising: a) ST-246 ranging from about 2 mg/ml to about 20 mg/ml; and b) hydroxypropyl-β-cyclodextrin content ranging from about 12.5 mg/ml to about 40 mg/ml.

The present invention also provides a process for preparing a water-soluble solid ST-246 pharmaceutical formulation comprising: a) mixing ST-246 with cyclodextrin in a pharmaceutically acceptable liquid carrier; and b) optionally filtering the mixture of step a); and c) lyophilizing said mixture.

DETAILED DESCRIPTION OF THE INVENTION

Figure 1:
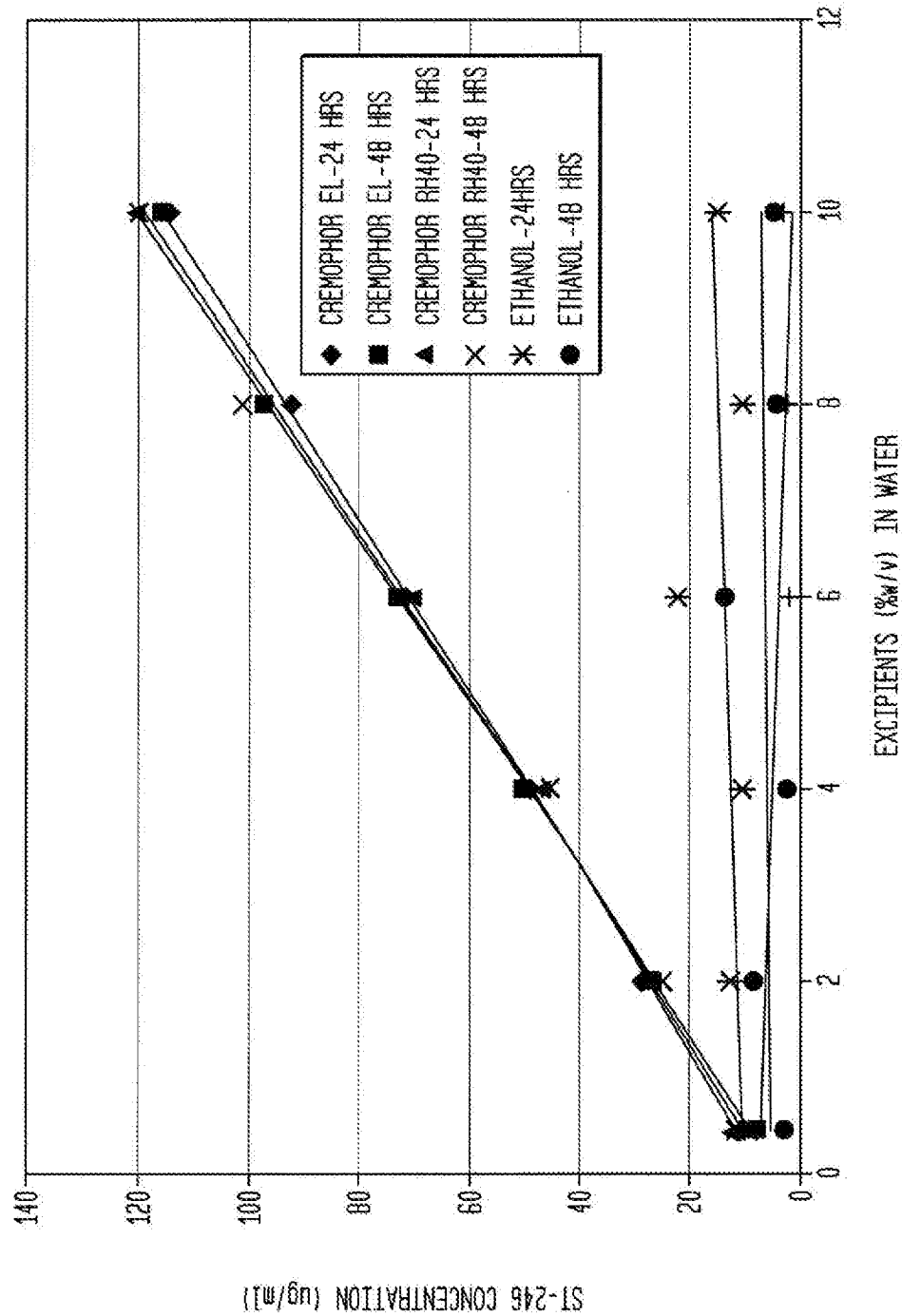
FIG. 1 depicts ST-246 solubility in aqueous solutions of excipients.

The present invention provides a safe and effective liquid pharmaceutical formulation comprising a therapeutically effective amount of ST-246 and cyclodextrin, and optionally further comprising one or more pharmaceutically acceptable ingredients selected from the group consisting of carrier, excipient, diluent, additive, filler, lubricant, solubilizer, preservative and binder. In one embodiment, cyclodextrin is hydroxypropyl-β-cyclodextrin. In another embodiment, hydroxypropyl-β-cyclodextrin has a degree of substitution between about 4 to about 8. In yet another embodiment, said cyclodextrin is sufobutyl ether-β-cylodextrin.

In one aspect of the invention, hydroxypropyl-β-cyclodextrin is present in amounts ranging from about 10% to about 50% by weight, more preferably about 20% to about 40% by weight. In yet another aspect of the invention, the liquid pharmaceutical formulation is adjusted to have pH between about 3 and 12, more preferably between about 3 and 10. In yet another aspect of the invention, the instant liquid pharmaceutical formulations are suitable for oral, parenteral, mucosal, transdermal or topical administration.

The invention also provides for methods of treating orthopoxvirus infections comprising administering to a subject in need thereof a liquid pharmaceutical formulation comprising a therapeutically effective amount of ST-246 and cyclodextrin and further comprising one or more pharmaceutically acceptable ingredients selected from the group consisting of carrier, excipient, diluent, additive, filler, lubricant and binder. In one embodiment, cyclodextrin is hydroxypropyl-β-cyclodextrin. In another embodiment, hydroxypropyl-β-cyclodextrin has a degree of substitution between about 4 to about 8. In yet another embodiment, cyclodextrin is sufobutyl ether-β-cylodextrin.

The instant methods also include a method of treating eczema vaccinatum comprising administering to a subject in need thereof a therapeutically effective amount of instant liquid formulation. According to the instant invention, the instant liquid pharmaceutical formulation can be administered via oral, parenteral, mucosal, transdermal or topical route of administration.

The instant invention also provides for a process of making instant liquid formulation comprising the steps of a) mixing ST-246 with cyclodextrin and b) optionally filtering the mixture of step a). The instant process comprises ST-246 which is selected from the group consisting of polymorphic Form I, Form II, Form III, Form IV, Form V and Form VI.

In one embodiment, cyclodextrin is hydroxypropyl-β-cyclodextrin. In another embodiment, hydroxypropyl-β-cyclodextrin has a degree of substitution between about 4 to about 8. In yet another embodiment, cyclodextrin is sufobutyl ether-β-cylodextrin.

In one aspect of the invention, the instant process comprises mixing ST-246 with cyclodextrin in a pharmaceutically acceptable liquid carrier for about 15 min to 72 hours. In another aspect of the invention, the instant process comprising mixing ST-246 with cyclodextrin in a pharmaceutically acceptable liquid carrier at a temperature range from about 28° C. to about 70° C. In one embodiment, the pharmaceutically acceptable liquid carrier is water.

In yet another aspect of the invention, a unit dosage liquid formulation is provided comprising: a) ST-246 content ranging from about 2 mg/ml to about 20 mg/ml; b) hydroxypropyl-β-cyclodextrin content ranging from about 12.5 mg/ml to about 40 mg/ml; and c) optionally comprising mannitol, trehalose dehydrate, lactose monohydrate, and purified water such that the total volume of the liquid formulation is about 100 ml. In one embodiment, the pH is adjusted to a range from about 3.0 to about 5.0 using 0.1 HCL/NaOH. In another embodiment, the pH is adjusted to a range from about 3.0 to about 5.0 using citrate buffer.

In yet another aspect of the invention, a unit dosage liquid formulation is provided comprising: a) ST-246 ranging from about 2 mg/ml to about 20 mg/ml; b) hydroxypropyl-β-cyclodextrin content ranging from about 12.5 mg/ml to about 40 mg/ml; and c) optionally comprising one or more pharmaceutically acceptable ingredient selected from the group consisting of: polyethylene glycol 400, polysorbate 80, polyethylene glycol 300, and purified water such that preferably, the total volume of the liquid formulation is about 100 ml. In one embodiment, a pH is adjusted to 3.0 to 5.0 using 0.1 HCL/NaOH. In another embodiment, the pH is adjusted to a range from about 3.0 to about 5.0 using citrate buffer.

Definitions

In accordance with this detailed description, the following abbreviations and definitions apply. It must be noted that as used herein, the singular forms "a," "an," and "the" include plural referents unless the context clearly dictates otherwise.

The term "pharmaceutical composition" or "pharmaceutical formulation" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions of the present invention encompass any composition made by admixing the active ingredient, active ingredient dispersion or composite, additional active ingredient(s), and pharmaceutically acceptable excipients.

The term "half-life" is a pharmacokinetic term used to indicate the length of time necessary to eliminate 50% of the remaining amount of drug present in the body.

The term "AUC" (i.e., "area under the curve," "area under the concentration curve," or "area under the concentration-time curve") is a pharmacokinetic term used to refer a method of measurement of bioavailability or extent of absorption of a drug based on a plot of an individual or pool of individual's blood plasma concentrations sampled at frequent intervals; the AUC is directly proportional to the total amount of unaltered drug in the patient's blood plasma. For example, a linear curve for a plot of the AUC versus dose (i.e., straight ascending line) indicates that the drug is being released slowly into the blood stream and is providing a steady amount of drug to the patient; if the AUC versus dose is a linear relationship this generally represents optimal delivery of the drug into the patient's blood stream. By contrast, a non-linear AUC versus dose curve indicates rapid release of drug such that some of the drug is not absorbed, or the drug is metabolized before entering the blood stream.

The term "$C_{max}$" (i.e., "maximum concentration") is a pharmacokinetic term used to indicate the peak concentration of a particular drug in the blood plasma of a patient.

The term "$T_{max}$" (i.e., "time of maximum concentration" or "time of $C_{max}$") is a pharmacokinetic term used to indicate the time at which the $C_{max}$ is observed during the time course of a drug administration. As would be expected, a dosage form that would include an immediate release as well as a gastric retentive component would have a $T_{max}$ that is higher than the $C_{max}$ for an immediate release dosage form, but lower than the $T_{max}$ for a purely gastric retentive dosage form.

As used herein, the term "subject" for purposes of treatment includes any subject, and preferably is a subject who is in need of treatment of an orthopoxvirus infection or related condition. The subject is typically an animal, more typically is a mammal. Preferably, the mammal is a human.

The term "chemically modified cyclodextrin" refers to one or more chemically modified cyclodextrins where there is independently more than one degree of substitution that can vary from about 0.5 to about 10.0. The degree of substitution (the mean number of functional groups per glucose unit) of the chemically modified cyclodextrin can vary as need to provide the necessary solubility and stability of the ST-246. For example, the degree of substitution can be between from about 0.5 to about 10.0. For a chemically modified cyclodextrin such as 2-hydroxypropyl-ß-cyclodextrin, the degree of substitution (of substituted hydroxy functional groups per glucose unit) can be, for example, between about 4.0 and 8.0. Degree of substitution can be determined by mass spectrometry (MS) or nuclear magnetic resonance (NMR) spectroscopy using known techniques.

The term "poorly soluble therapeutic agent" refers to a compound having biological activity and a solubility in water of less than about 1 mg/mL in buffer of pH 1.2 to 7 at 20° C. 25 C and 37 degree. In certain embodiments, the poorly soluble therapeutic agent is an organic compound that has a molecular weight of less than 1500 g/mol, and preferably less than 500 g/mol. In certain embodiments, the poorly soluble therapeutic agent is a compound, for example, an organic compound, having an aqueous solubility of less than about 0.5 mg/mL, less than about 0.3 mg/mL, or less than about 0.1 mg/mL, at pH 7 and 20° C.

As used herein, "therapeutically effective amount" refers to an amount of ST-246 that is nontoxic but sufficient in preventing or ameliorating the severity of orthopoxvirus infection or related condition.

As used herein, "percent," "percentage" or the symbol "%" means the percent of the component indicated in the composition based on the amount of the carrier present in the composition, on a weight/weight (w/w), weight/volume (w/v) or volume/volume (v/v) concentration, as indicated with respect to any particular component, all based on the amount of the carrier present in the composition. Thus, different types of carriers can be present in an amount of up to 100% as indicated, which does not preclude the presence of the API, the amount of which can be indicated as a % or as a certain number of mg present in the composition or a certain number of mg/mL present, where the % or mg/mL is based on the amount of the total carrier present in the composition. Certain types of carriers can be present in combination to make up 100% of the carrier.

A term "pharmaceutically acceptable carrier" as used herein is non-toxic or has certain toxic attributes that are not dose limiting to achieve therapeutic advantages to recipients at the dosages and concentrations required and is compatible with other ingredients of the formulation.

The term "pharmaceutically acceptable excipient," includes vehicles, adjuvants, or diluents or other auxiliary substances, such as those conventional in the art, which are readily available to the public, and which are non-toxic or have acceptable toxicities to recipients at the dosages and concentrations employed, and is compatible with other ingredients of the formulation. For example, pharmaceutically acceptable auxiliary substances include pH adjusting and buffering agents, tonicity adjusting agents, stabilizers, preservatives, solubilzers, wetting agents and the like.

Cyclodextrins

Cylodextrins are water soluble sugar oligomers. Many different cyclodextrins exist and are distinguished from each other by the number of glucopyranose units. The most common cyclodextrins are composed of six, seven or eight alpha-D-glucose units. Cyclodextrins form structures having cavities which are hydrophilic on the outside and lipophilic on the inside. The number of glucose units determines the size of the cavity. The hydrophilic exterior gives cyclodextrins their solubility in aqueous solutions while the lipophilic interior or cavity provides an environment which is often attractive to other hydrophobic molecules. By sequestering the drug in the hydrophobic core, it is solubilized with the cyclodextrin molecule so forming an aqueous soluble complex. Cyclodextrins can take up the entirety of a molecule or only a part thereof into the cavity. The stability of the resulting complex depends on how well the drug molecule fits into the cyclodextrin cavity.

There is still a high degree of unpredictability with regards to whether cyclodextrins will improve the solubility of a particular drug, such as for example ST-246. Unexpectedly, a novel liquid formulation comprising cyclodextrins has been identified which is shown to provide adequate solubility of ST-246 and which could be delivered to subjects in safe and effective manner.

Cyclodextrins suitable for use in the compositions, formulations, and methods herein disclosed are generally cyclic oligosaccharides with a cone-like shape. The interior of the cone acts as a hydrophobic cavity, while the exterior of the cone is hydrophilic. The former property enables cyclodextrins to form inclusion complexes with a wide variety of lipophilic molecules or portions thereof, which "fit" into the cavity while the latter property facilitates aqueous solubility. Cyclodextrin derivatives have been extensively studied for use as parenteral drug carriers owing to their high water solubility and low toxicity. (Fromming & Szejtli, J. (1994).

Chemically Modified Cyclodextrins

The cyclodextrin suitable for use in the compositions, formulations, and methods herein disclosed preferably are chemically modified cyclodextrins. The chemically modified cyclodextrins can include derivatives of α-cyclodextrin, β-cyclodextrin, Gamma cyclodextrin or δ-cyclodextrin. The chemically modified cyclodextrins can include, but are not limited to methyl-β-cyclodextrin, 2-6-di-O-methyl-β-cyclodextrin, randomly methylated-β-cyclodextrin, ethyl-β-cyclodextrin, carboxymethyl-β-cyclodextrin, diethylaminoethyl-β-cyclodextrin, 2-hydroxypropyl-β cyclodextrin, 3-hydroxypropyl-β-cyclodextrin, 2,3-dihydroxypropyl-β-cyclodextrin, and sulfobutyl ether-β-cyclodextrin. Preferably, the chemically modified cyclodextrin is 2-hydroxypropyl-β-cyclodextrin, 3-hydroxypropyl-β-cyclodextrin, 2,3-dihydroxypropyl-β-cyclodextrin, and sulfobutyl ether-β-cyclodextrin. More preferably, the chemically modified cyclodextrin is 2-hydroxypropyl-β-cyclodextrin or sulfobutyl ether-β-cyclodextrin. Preferably, the degree of substitution for 2-hydroxypropyl-β-cyclodextrin is between 4 and 8.

The preparation of pharmaceutical formulations as herein disclosed involves dissolving the chemically modified cyclodextrin in a suitable volume of aqueous carrier medium (for example, water for injection), removal of oxygen (for example, with nitrogen, inert gas, or freeze-thaw under vacuum), followed by the gradual addition of ST-246 to the cyclodextrin solution under vigorous stirring until essentially all of the ST-246 has been complexed and is in solution. The temperature of the cyclodextrin solution can be between 0° C.-80° C. Preferably the temperature of the cyclodextrin solution is maintained between about 2° C.-70° C. degrees.

After addition of the ST-246, the solution can be brought to a final volume with de-oxygenated aqueous carrier medium. The solution can then be sterilized, for example, by filtration and/or aseptically transferred to vials or ampoules. The solution can be transferred directly to ampoules for sterilization by autoclaving or irradiation. The vials or ampoules can be sealed under an inert gas, such as nitrogen. The molar ratio of ST-246 to chemically modified cyclodextrin can be for example about 0.03 mol/mol. Preferably, the molar ratio of ST-246 to chemically modified cyclodextrin is about 0.01 to about 1.0. More preferably, the molar ratio of ST-246 to chemically modified cyclodextrin is about 0.03 to 0.15 mol/mol.

Pharmaceutical Compositions

Pharmaceutical compositions and single unit dosage forms comprising a compound of the invention, or a pharmaceutically acceptable polymorph, prodrug, salt, solvate, hydrate, or clathrate thereof, are also encompassed by the invention. Individual dosage forms of the invention can be suitable for oral, mucosal (including sublingual, buccal, rectal or nasal), parenteral (including subcutaneous, intramuscular, bolus injection, intraarterial, or intravenous), transderal, and topical administration.

Pharmaceutical compositions and dosage forms of the invention comprise a compound of the invention, or a pharmaceutically acceptable prodrug, polymorph, salt, solvate or hydrate thereof. Specifically, it had been previously shown in U.S. Ser. No. 61/316,747, which is incorporated herein by reference, that ST-246 exists in different crystalline forms denominated Form I, Form II, Form III, Form IV, Form V, and Form VI. It had also been discovered that Form I is a monohydrate crystalline form of ST-246 which shows an X-ray powder diffraction pattern having characteristic peaks at a reflection angle 2θ of about:

7.63, 10.04, 11.47, 14.73, 15.21, 15.47, 16.06, 16.67, 16.98, 18.93, 19.96, 20.52, 20.79, 22.80, 25.16, 26.53, 27.20, 27.60, 29.60, 30.23, 30.49, 30.68, 31.14, 33.65, 34.33, 35.29, 35.56, 36.30, 37.36, 38.42, 38.66 degrees.

It had also been shown that Form II is an anhydrate crystalline form of ST-246. Form II shows an X-ray powder diffraction pattern having characteristics according to FIG. 12.

It had been further shown that Form III is a monohydrate crystalline form of ST-246 which shows an X-ray powder diffraction pattern having characteristic peaks at a reflection angle 2θ of about:

6.71, 9.05, 12.49, 13.03, 13.79, 14.87, 15.72, 16.26, 16.74, 18.10, 18.43, 19.94, 21.04, 21.51, 23.15, 23.51, 25.32, 26.24, 26.87, 27.32, 27.72, 28.55, 29.08, 29.50, 29.84, 31.27, 33.48, 35.36, 39.56 degrees.

Figure 13:
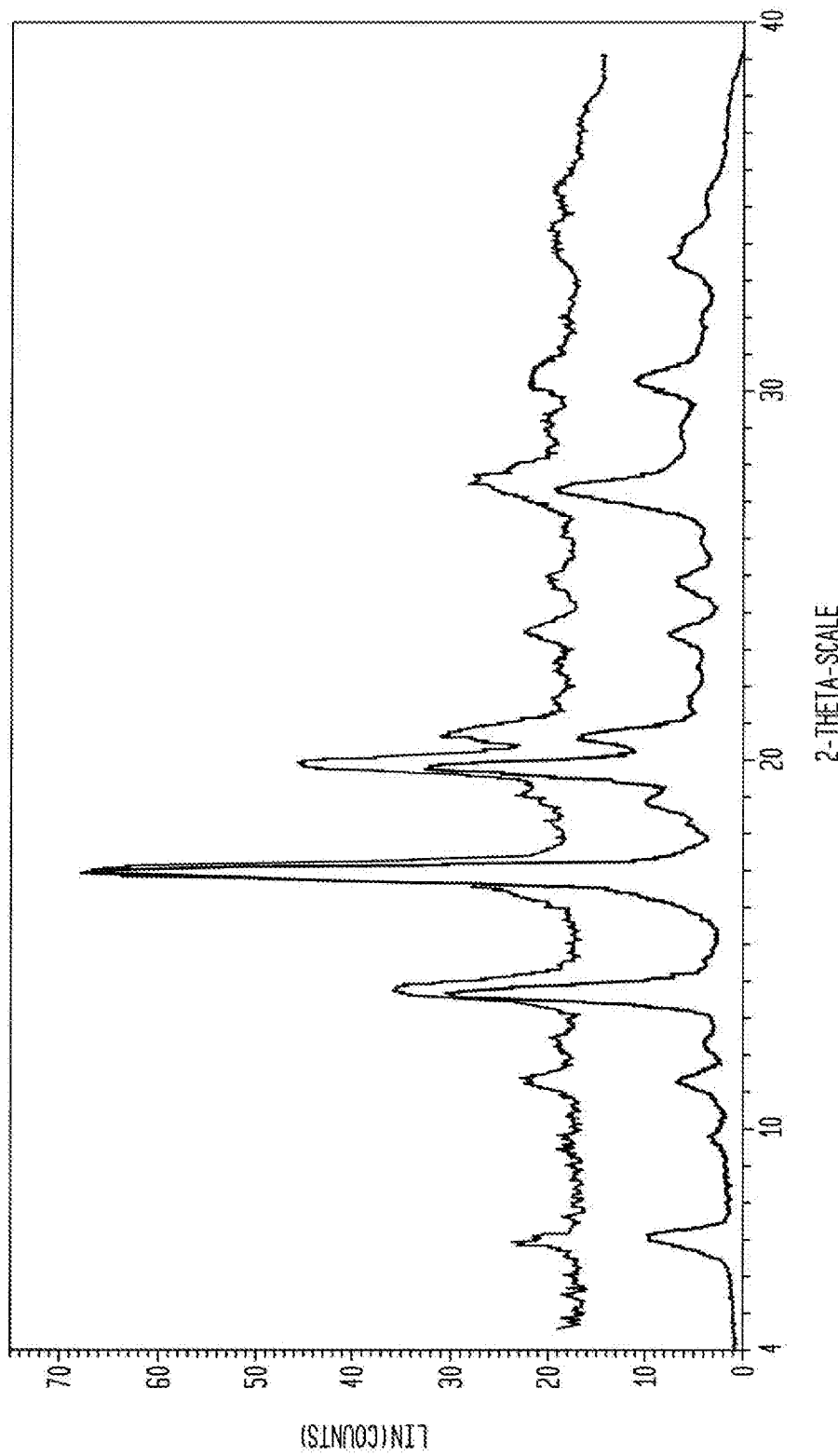
FIG. 13 shows two X-ray powder diffraction (XRPD) patterns of Form IV (from two different samples).

It had been further show that Form IV is an anhydrate crystalline form of ST-246. Form IV shows an X-ray powder diffraction pattern having characteristics according to FIG. 13.

Figure 14:
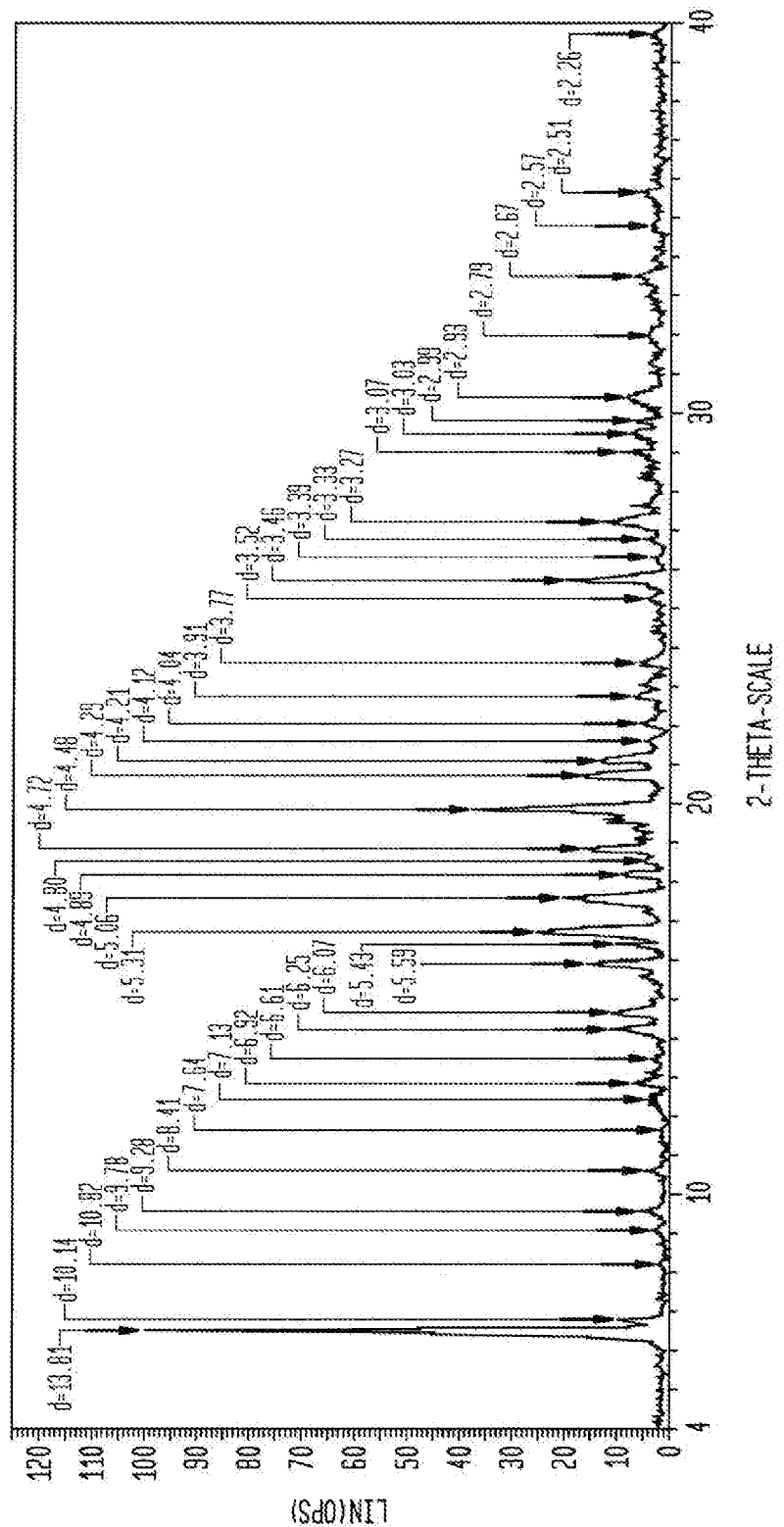
FIG. 14 shows an X-ray powder diffraction (XRPD) pattern of Form V.

Further, it had been shown that Form V is a hemihydrate crystalline form of ST-246. Form VI shows an X-ray powder diffraction pattern having characteristics according to FIG. 14.

Figure 15:
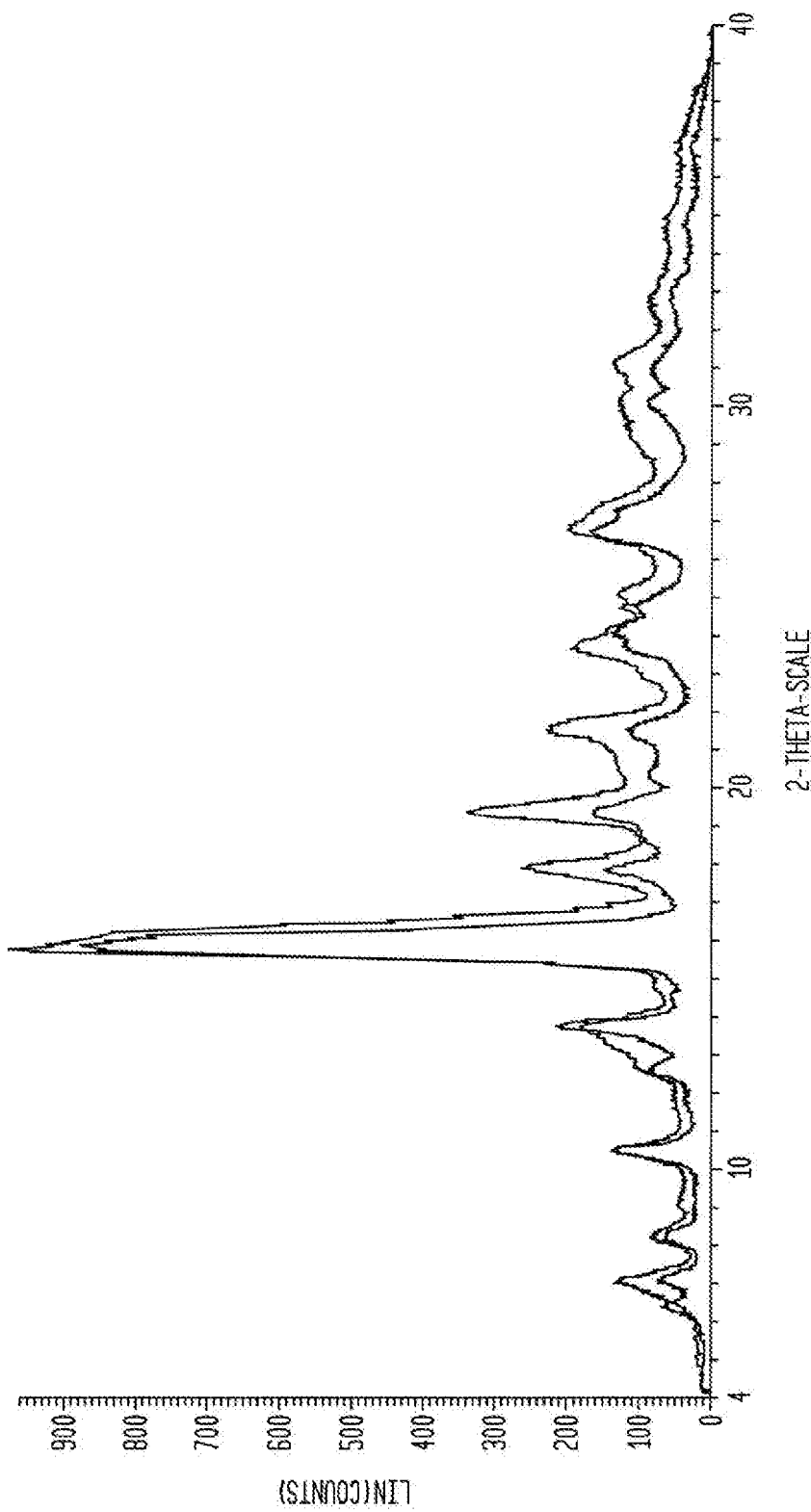
FIG. 15 shows an X-ray powder diffraction (XRPD) patterns of Form VI (from two different samples).

It had also been shown that Form VI is a monohydrate crystalline form of ST-246. Form VI shows an X-ray powder diffraction pattern having characteristics according to FIG. 15.

ST-246 Form I is the preferred polymorph of ST-246. It appears to be the thermodynamically most stable form, as all other get converted to Form-I.

ST-246 Form I is stable and hence can be stored at ambient conditions. Form I has not been shown to convert to another polymorphic form under several environmental and process conditions that a drug could experience during various stages of manufacturing and storage. Some of the conditions tested include storage at high temperature and high humidity, room temperature and high humidity, low humidity, up to 60° C., capsule manufacturing using wet granulation and drying, during milling or micronization process, in suspension, long term storage at room temperature. Further, Form-I is non hygroscopic and hence does not absorb moisture even at 90% relative humidity conditions. Form I is reliably manufactured by the commercial crystallization process with more than 99.0% purity and with any single impurities not more than 0.15%. The instant Examples describe experiments with ST-246 Form I. However, ST-246 Form II, Form III, Form IV and Form V can be used to obtain similarly stable liquid ST-246 formulations.

Pharmaceutical compositions of the invention that are suitable for oral administration can be presented as discrete dosage forms, such as, but are not limited to capsules and liquids (e.g., flavored syrups). Such dosage forms contain predetermined amounts of active ingredients, and can be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof.

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal and topical dosage forms of the invention include, but are not limited to, creams, lotions, ointments, gels, solutions, emulsions, suspensions, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Intravenous Administration, Dosage and Duration

As indicated below in Example 4, a population PK model was developed to assess the disposition of ST-246 following IV infusion in male and female uninfected cynomolgus monkeys. A three-compartment model with dose as covariate described the nonlinear PK (reduced clearances at higher doses) of IV ST-246. Diagnostic plots and a visual predictive check confirmed that the observed data were reasonably well described by the proposed model. Allometric scaling of PK parameters in monkeys was performed to determine PK parameters in humans.

A targeted range of exposure was determined a priori based on observed concentration-time profiles in human subjects treated with oral ST-246. Monte Carlo simulations were performed to determine candidate dosing levels of IV ST-246 that would results in similar AUC, $C_{max}$, and $C_{min}$ values as those previously observed in healthy uninfected humans following repeated oral administration of 400 and 600 mg ST-246. Numerous different possible dosing regimens were simulated. Predicted AUC and $C_{max}$ values were compared first to those observed after oral doses. $C_{min}$ values were compared thereafter. In general, a regimen that can generate equivalent $C_{min}$ would require longer infusion time with higher AUC values than the regimen that generates equivalent AUC and $C_{max}$.

Repeated IV infusion of 115 mg QD over 5 hours or 65 mg BID over 1 hour would provide AUC and $C_{max}$ values at steady state very similar to those observed after oral doses of 400 mg. Repeated IV infusion of 80 mg BID over 2 hours resulted in $C_{min}$ values at 12 and 24 hours similar to those observed following oral administration of 400 mg QD in healthy uninfected humans. Similarly, repeated IV infusion of 145 mg QD over 4 hours or 95 mg BID over 1 hour would provide AUC and $C_{max}$ values at steady state very similar to those observed after oral doses of 600 mg. Finally, repeated IV infusion of 85 mg BID over 1 hour resulted in $C_{min}$ values at 12 and 24 hours similar to those observed following oral administration of 600 mg QD in healthy uninfected humans.

Accordingly, in one embodiment of the invention, the instant liquid pharmaceutical formulation can be administered intravenously. Preferably, about 50 to about 500 mg, more preferably about 200 mg to about 400 mg, most preferably about 300 mg of ST-246 is infused per single session of intravenous administration. In another embodiment, the treatment is carried out for a period ranging from about 7 to about 30 days, preferably, about 7 to about 15 days. In yet another embodiment, the duration of each session of intravenous administration is from about 2 to about 24 hours. In a further embodiment, the treatment carried out continuously over the course of treatment at a dosage of about 50 to about 500 mg of ST-246 per day. Alternatively, the treatment may be carried out during two sessions per day, wherein the duration of each session is from about 2 to about 12 hours.

Example 1—ST-246 Solubility Studies in Various Excipients—Solubility in Water, Oily Vehicles, Surfactants and Co-Solvents ST-246, an anti-smallpox small molecule and is intended to be administered by various routes of administration, is poorly soluble in water and in pharmaceutically acceptable pH buffers in the range of 2-11. The preferred formulation for injectable formulation is a liquid formulation prepared using pharmaceutically acceptable additives. To obtain liquid formulation, the solubility of the drug should be such that therapeutically effective amount of drug can be delivered safely. Further, the formulation should be able to withstand dilution in commonly used intravenous dilution fluids such as normal saline and in blood upon injection. Since ST-246 is an insoluble drug, it poses challenges to development of safe and effective IV solution formulation.

Unexpectedly, a composition has been identified which provides adequate solubility of ST-246 and can be delivered to subjects in safe and effective manner.

For these experiments, varies cosolvents and surfactants were investigated for solubilization of ST-246. For these experiments, ST-246 polymorphic Form I was used. The solutions of cosolvents included polyethylene glycol (PEG) 400, propylene glycol, ethanol; the solutions of surfactants included polyethoxylene castor oil, polyoxyethylene hydrogenated castor oil (Cremophor® EL and RH 40) polysorbates (Tween® series of surfactants) and Solutol® HS, a polyethoxylated fatty alcohol and the polyglycolysed glyceride, Labrasol®. In addition, the solubility of ST-246 in several oils including sesame oil, soybean oil and corn oil was investigated. The results of the solubilization experiments are shown in Table 1 and summarized below.

TABLE 1

Solubility of ST246 Form I Monohydrate in Various Excipients

| Excipients | ST-246 Solubility (mg/mL) | Excipient Description |
|---|---|---|
| Phosphate Buffer, pH6.8 | <0.1, Insoluble | |
| Water | <0.1, Insoluble | |
| 0.01N HCl | <0.1, Insoluble | |
| PEG 400 | 127 | Polyethylene glycol |
| Labrasol | 82 | Caprylocaproyl Polyoxylglycerides |
| Ethanol | 75 | |
| Propylene Glycol | 43 | |
| Tween 80 | 22 | Polysorbate 80 |
| Cremophor EL | 17 | Polyoxyethylated castor oil |
| Cremophor RH-40 | 17 | Glycerol-polyethylene glycol oxystearate Castor oil |
| Plurol Oleique | 6 | Polyglyceryl Oleate |
| Lauroglycol FCC | 4 | Propylene glycol monolaurate |
| Labrafil IL M | 3 | Lauroyl polyoxylglycerides |
| Labrafac Lipophile | 2 | Medium Chain Triglycerides |
| Sesame oil | 1 | |
| Soy oil | 1 | |
| Oils | <1 | Flax, Corn, Olive |

Figure 2:
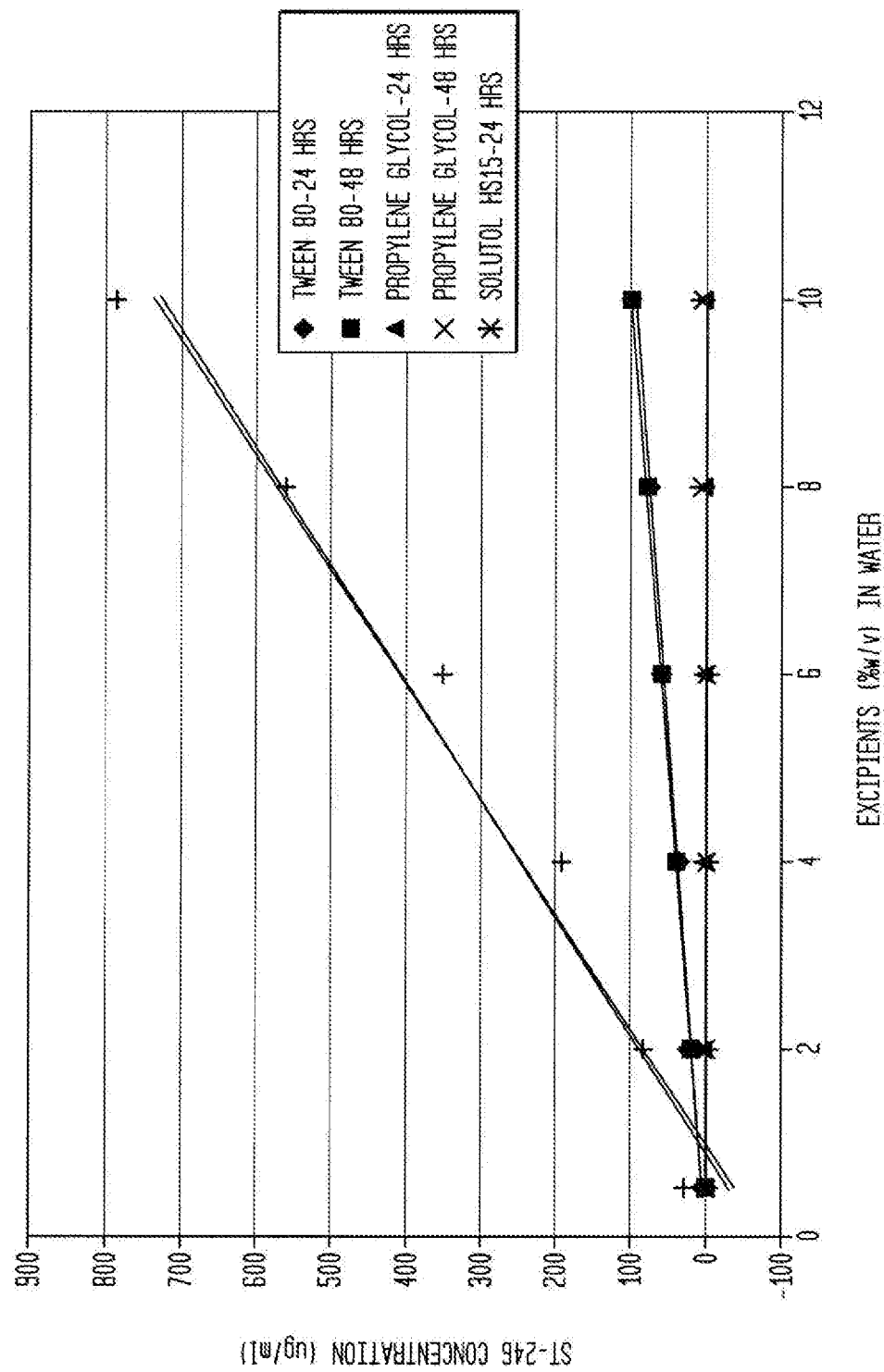
FIG. 2 depicts solubility ST-246 in aqueous solution of excipients.
Figure 3:
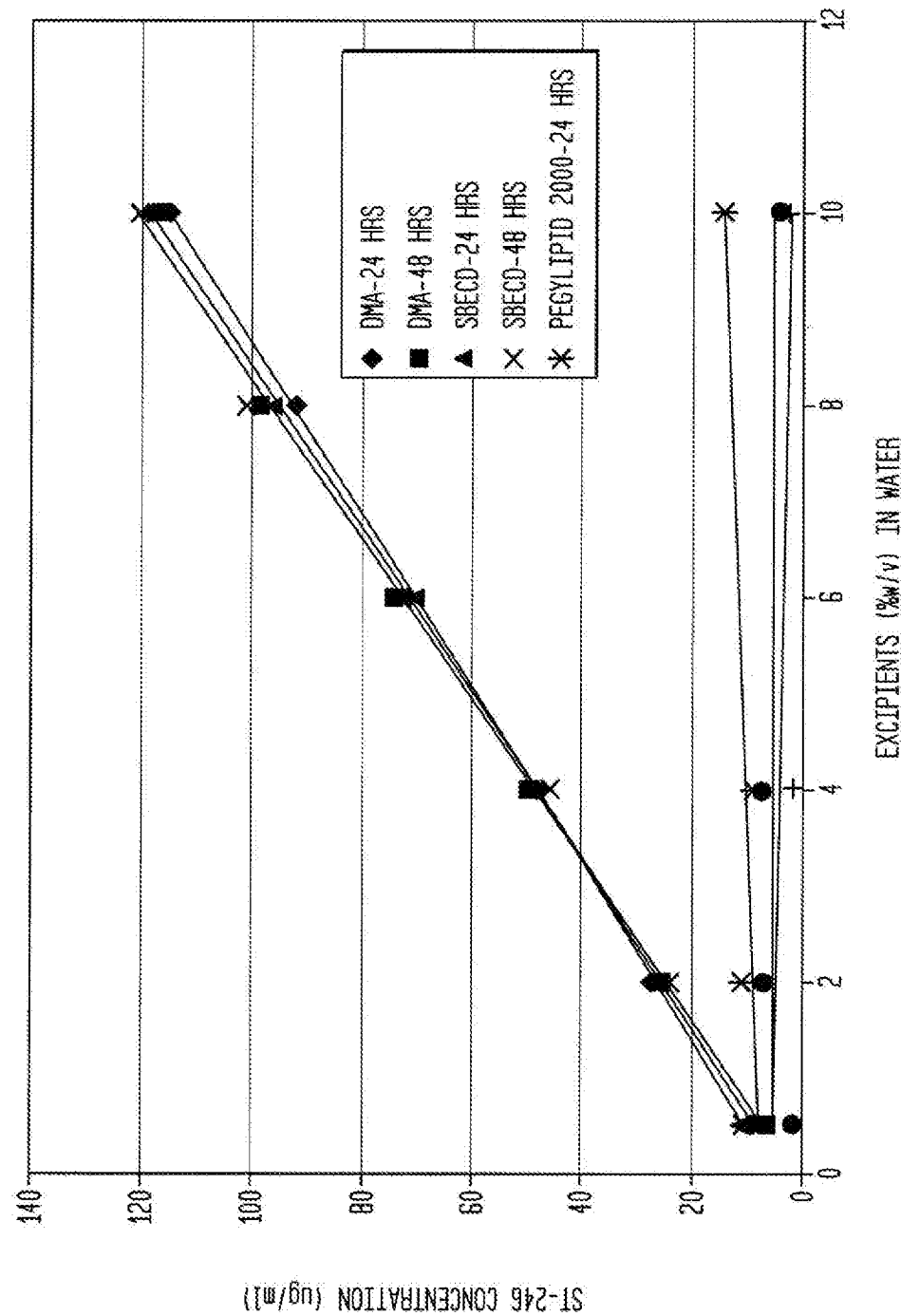
FIG. 3 depicts solubility of ST-246 in aqueous solutions of excipients

As shown in Table 1, PEG 400 demonstrated the greatest ST-246 solubilization followed by Labrasol®, ethanol, Propylene Glycol, Tween 80, Cremophor EL and Cremophor RH-40, all of which were identified as potential intravenous formulation candidates. Thus, based upon the solubility data, PEG 400 and ethanol were selected for cosolvent combination analysis. The absolute solubility of ST-246 in oils was less than 5 mg/ml eliminating them as possible IV formulation candidates.

Based on the results of these experiments, a multitude of formulations containing the selected excipients at varying concentrations were created. Thus, the instant formulations were diluted with IV dilution fluid, 5% dextrose and 0.05 mM, pH 7.5, Phosphate buffer to make sure that formulation withstand dilution at least for 12 hours. The results obtained established that all of the combinations tested were sub-optimal for a prolonged IV infusion. Even when the quantity of ST-246 was reduced from 10 mg/mL to 5 mg/mL the solution stability was extended by less than 2 hrs indicating that cosolvents and surfactants likely would not yield an IV formulation suitable for ST-246. These results can be found in Table 2.

TABLE 3

Composition of ST-246 in Aqueous Solutions of Excipients (0.5 to 10% w/v)

| Excipient | % w/v in $H_2O$ | μg/ml ST-246 24 hrs | μg/ml ST-246 48 hrs |
|---|---|---|---|
| Cremophor EL | 0.5 | 10 | 8 |
| | 2.0 | 28 | 26 |
| | 4.0 | 48 | 49 |
| | 6.0 | 71 | 74 |
| | 8.0 | 92 | 98 |
| | 10.0 | 115 | 116 |
| Cremophor RH 40 | 0.5 | 12 | 10 |
| | 2.0 | 26 | 25 |
| | 4.0 | 47 | 46 |
| | 6.0 | 71 | 72 |
| | 8.0 | 96 | 101 |
| | 10.0 | 120 | 120 |
| Ethanol | 0.5 | 8 | 3 |
| | 2.0 | 12 | 8 |
| | 4.0 | 10 | 2 |
| | 6.0 | 22 | 14 |
| | 8.0 | 10 | 4 |

TABLE 2

Co-solvent Combinations Containing 5 mg/ml ST-246 in 5% w/v Dextrose and in PBS

| Sample ID | % Total Volume | Excipient | Density (g/cc) | Weight (g) | ST-246 concentration mg/ml | Dilution Shelf Life Stability Hours in 5% Dextrose 1:1 | 1:5 | 1:10 | Dilution Shelf Life Stability Hours in 50 mM PBS, pH 7.4 1:1 | 1:2 | 1:15 |
|---|---|---|---|---|---|---|---|---|---|---|---|
| A | 50% | Cremophor EL | 1.05 | 2.625 | 5 | 3 | 3 | 3 | 1 | 0.5 | 1 |
| | 50% | Ethanol | 0.789 | 1.973 | | | | | | | |
| B | 20% | Cremophor RH 40 | 1.06 | 1.060 | 5 | 0.5 | 0.5 | 0.5 | 1 | 0.5 | 1 |
| | 80% | Ethanol | 0.789 | 3.156 | | | | | | | |
| C | 60% | PEG-400 | 1.127 | 3.381 | 5 | ND | ND | ND | 0.25 | 0.25 | 0.25 |
| | 30% | Ethanol | 0.789 | 1.184 | | | | | | | |
| | 10% | Tween-80 | 1.064 | 0.532 | | | | | | | |
| D | 60% | Cremophor EL | 1.05 | 3.150 | 5 | 3 | 3 | 3 | 0.17 | 0.5 | 0.5 |
| | 35% | Ethanol | 0.789 | 1.381 | | | | | | | |
| | 5% | Tween-80 | 1.064 | 0.266 | | | | | | | |
| E | 60% | Cremophor RH 40 | 1.06 | 3.180 | 5 | 3 | 18 | 18 | 0.25 | 0.5 | 0.5 |
| | 35% | PEG-400 | 1.127 | 1.972 | | | | | | | |
| | 5% | Ethanol | 0.789 | 0.197 | | | | | | | |
| F | 35% | Cremophor RH 40 | 1.06 | 1.855 | 5 | 3 | 3 | 3 | 0.08 | 0.5 | 0.5 |
| | 60% | PEG-400 | 1.127 | 3.381 | | | | | | | |
| | 5% | Ethanol | 0.789 | 0.197 | | | | | | | |
| G | 30% | Cremophor RH 40 | 1.06 | 1.590 | 5 | 3 | 3 | 3 | 0.17 | 0.33 | 0.33 |
| | 30% | PEG-400 | 1.127 | 1.691 | | | | | | | |
| | 40% | Ethanol | 0.789 | 1.578 | | | | | | | |
| H | 30% | Cremophor RH 40 | 1.06 | 1.590 | 5 | 3 | 3 | 1 | 0.08 | 0.5 | 0.5 |
| | 40% | PEG-400 | 1.127 | 2.254 | | | | | | | |
| | 30% | Ethanol | 0.789 | 1.184 | | | | | | | |
| I | 40% | Cremophor RH 40 | 1.06 | 2.120 | 5 | 3 | 3 | 3 | ND | 0.25 | 0.5 |
| | 30% | PEG-400 | 1.127 | 1.691 | | | | | | | |
| | 30% | Ethanol | 0.789 | 1.184 | | | | | | | |

Example 2—Composition of ST-246 in Carious Concentrations of Cosolvents/Surfactant in Water Based upon the solubility data obtained from the neat formulation as described in Example 1, further formulation studies of ST-246 were performed in conjunction with selected excipients diluted to various concentrations. These results are summarized in Table 3. For these experiments, the analyzed excipients included Cremophor EL, Cremophor RH-40, Ethanol and PEG 400. The concentrations were determined by HPLC analysis at 24 hours and 48 hours.

TABLE 3-continued

Composition of ST-246 in Aqueous Solutions of Excipients (0.5 to 10% w/v)

| Excipient | % w/v in $H_2O$ | μg/ml ST-246 24 hrs | μg/ml ST-246 48 hrs |
|---|---|---|---|
| | 10.0 | 15 | 5 |
| | 0.5 | 6 | 8 |
| | 2.0 | 8 | 7 |
| | 4.0 | 2 | 2 |
| | 6.0 | 2 | 2 |
| | 8.0 | 2 | 2 |
| | 10.0 | 3 | 3 |

Further, additional excipients investigated included two types of cyclodextrins (HP-ß-CD and SBECD), two types of pegylated phospholipids with different molecular weights (i.e PEG-Phospholipid-2000 and PEG Phospholipid-5000) as well as the surfactants Tween 80 and Solutol HS and the solvents Propylene glycol and Dimethyl acetamide (DMA). Aqueous solutions of these excipients were prepared at a concentration range of 0.5 to 10% w/v in water and solubility of ST-246 in these solutions was determined by HPLC analysis at 24 and 48 hours. The results of these experiments are summarized in Table 4 and FIGS. 1, 2 and 3.

TABLE 4

Composition of ST-246 in Aqueous Solutions of Excipients (0.5 to 10% w/v)

| Excipient | % w/v in H$_2$O | µg/ml ST-246 24 hrs | µg/ml ST-246 48 hrs |
|---|---|---|---|
| DMA | 0.5 | 9 | 7 |
|  | 2.0 | 12 | 10 |
|  | 4.0 | 2 | 2 |
|  | 6.0 | 6 | 5 |
|  | 8.0 | 2 | 2 |
|  | 10.0 | 3 | 3 |
| Sulfylbutylether CD | 0.5 | 22 | 19 |
|  | 2.0 | 45 | 43 |
|  | 4.0 | 66 | 65 |
|  | 6.0 | 99 | 96 |
|  | 8.0 | 138 | 148 |
|  | 10.0 | 186 | 177 |

TABLE 4-continued

Composition of ST-246 in Aqueous Solutions of Excipients (0.5 to 10% w/v)

| Excipient | % w/v in H$_2$O | µg/ml ST-246 24 hrs | µg/ml ST-246 48 hrs |
|---|---|---|---|
| PEG Phospholipid-2000 | 0.5 | 8 | 8 |
|  | 2.0 | 21 | 21 |
|  | 4.0 | 38 | 40 |
|  | 6.0 | ND | ND |
|  | 8.0 | ND | ND |
|  | 10.0 | 103 | 97 |
| PEG Phospholipid-2000 | 0.5 | 5 | 4 |
|  | 2.0 | 11 | 10 |
|  | 4.0 | 25 | 27 |
|  | 6.0 | ND | ND |
|  | 8.0 | ND | ND |
|  | 10.0 | 66 | 60 |

Further, the data obtained from solubility of ST-246 in various vehicles in water was used to analyze solubilization efficiency of each excipient. Table 5 below is a summary of the solubilization efficiency as measured by the slope of the trend lines of ST-246 concentration plotted against % w/v of the excipients in water; the larger the slope, the greater the solubilization efficiency. The excipients are ranked in order based upon the magnitude of the solubilization efficiency with the excipient with the highest ST-246 solubilization efficiency in aqueous solutions ranked as number one. Column 5 represents the solubility of ST-246 determined in mg/ml in pure (neat 100%) excipients.

TABLE 5

Summary of ST-246 Solubilization in Aqueous Solutions of Excipients

| Excipient | Solubility Curve Slope (24 hrs) | Solubility Curve Slope (48 hrs) | Solubilization Efficiency Rank Order (slope of trend line) | ST-246 Solubility in Neat Excipient (mg/ml) |
|---|---|---|---|---|
| HPBCD | y = 79.909x − 69.594<br>R2 = 0.97 | y = 81.46x − 77.217<br>R2 = 0.97 | 1 | ~0.8/ml in 10% w/w HPBCD solution in water |
| SBECD | y = 13.627x + 15.477<br>R2 = 0.99 | y = 16.884x = 5.359<br>R2 = 0.98 | 2 | ~0.18 in 10% SBECD solution in water |
| Cremophor RH 40 | y = 11.485x + 3.64<br>R2 = 0.998 | y = 11.953x + 1.4409<br>R2 = 0.997 | 3 | 17 |
| Cremophor EL | y = 10.979x + 4.8813<br>R2 = 0.999 | y = 11.503x + 3.4726<br>R2 = 0.998 | 4 | 17 |
| Tween80 | y = 10.338x + 0.8229<br>R2 = 0.9985 | y = 9.905x + 0.816<br>R2 = 0.9995 | 5 | 22 |
| PEG Phospholipid-2000 | y = 10.138x + 0.7815<br>R2 = 0.998 | y = 9.425x + 2.606<br>R2 = 1.00 | 6 | NA (solid) |
| Solutol HS 15 | y = 9.4708x + 1.105<br>R2 = 0.9993 | y = 9.217x + 0.6869<br>R2 = 0.9994 | 7 | Not done |
| PEG Phospholipid-5000 | y = 6.5811x − 0.5495<br>R2 = 0.996 | y = 6.0211x + 0.2705<br>R2 = 0.9954 | 8 | NA (solid) |
| Ethanol | y = 0.5619x + 10.025<br>R2 = 0.1676 | y = 0.1022x + 5.3352<br>R2 = 0.0079 | 9 | 75 |
| PG | y = −0.004x + 3.0472<br>R2 = 0 | y = 0.0235x + 1.4007<br>R2 = 0.0291 | 10 | 43 |
| PEG 400 | y = −0.4758x + 6.1872<br>R2 = 0.4717 | y = −0.5856x + 6.8136<br>R2 = 0.5844 | 11 | 127 |

TABLE 5-continued

Summary of ST-246 Solubilization in Aqueous Solutions of Excipients

| Excipient | Solubility Curve Slope (24 hrs) | Solubility Curve Slope (48 hrs) | Solubilization Efficiency Rank Order (slope of trend line) | ST-246 Solubility in Neat Excipient (mg/ml) |
|---|---|---|---|---|
| DMA | y = −0..8313x + 10.026<br>R2 = 0.566 | y = −0.6674 = 8.256<br>R2 = 0.5437 | 12 | ND |

ND = Not done

Comparison of columns 4 and 5 in Table 5 reveals that the excipient in which ST-246 has the highest solubility (column 5) does not necessarily correspond to the solubility of ST-246 of that excipient diluted with water (column 4). The data obtained from the solubilization experiments demonstrated the highest solubilization efficiency was demonstrated by the two cyclodextrins with HP-ß-CD being the most efficient followed by SBECD. Among all the surfactants tested, the CremophorEL and Cremophor RH-40 exhibited maximum solubilization capacity followed by Polysorbate 80. Between the two PEG phospholipids, PEG phospholipid-2000 was a better solubilizer than PEG phospholipid-5000.

Example 3—ST-246 Solubility with Complexing Agents

Figure 4:
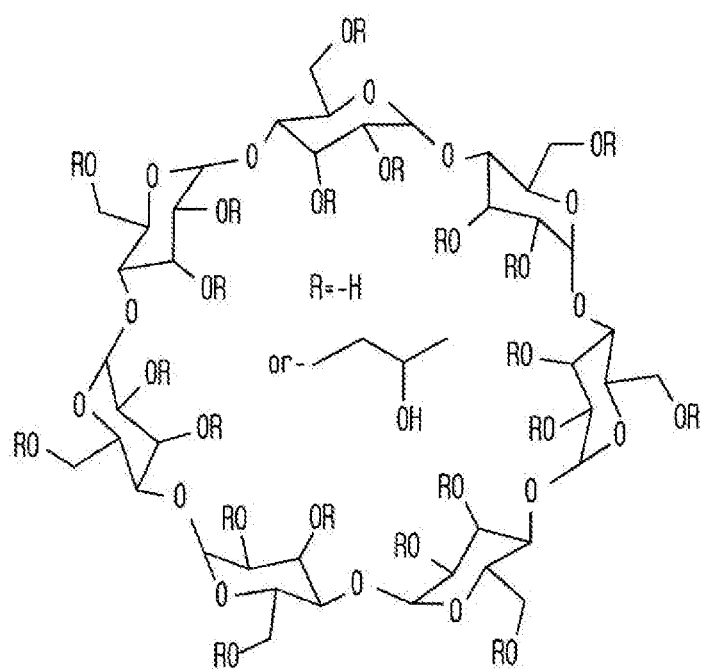
FIG. 4 depicts hydroxypropyl-β-cyclodextrin (HP-ß-CD) structure.

Further experiments investigated solubility of ST-246 in cyclodextrins. Cyclodextrins contain a torus-shaped ring with a polar hydrophilic outside and an apolar hydrophobic cavity. FIG. 4 illustrates the structure of one type of cyclodextrin, hydroxypropyl-β-cyclodextrin (HP-β-CD) and Table 6 provides characteristics summary of cyclodextrins.

TABLE 6

Characteristics of cyclodextrins

| Generic name | 2-hydroxypropyl-β-cyclodextrin |
|---|---|
| Appearance | White amorphous powder |
| Average molecular weight | 1380-1480 daltons |
| Aqueous solubility (g/100 mL): | |
| at 25° C. | 65% |
| at 50° C. | 80% |
| Decomposition temperature | Above 300° C. |
| Sterilization | Autoclaving at 121° C. possible |

Further, Table 7 summarizes solubility of ST-246 in aqueous solutions of various grades of cyclodextrins at concentrations ranging from 20 to 40%. As shown in Table 7, the range of ST-246 solubilized by cyclodextrin was 1.5 to 11 mg/ml at 37° C., with HP-ß-CD out-performing sulfobutylether-derivatized cyclodextrin (SBECD). The data obtained from the complexation experiments supported HP-ß-CD as a potential candidate for the intravenous formulation.

TABLE 8

Solubility of ST-246 in Aqueous Solutions of Substituted β-Cyclodextrins at 37° C.

| Substituted beta-CD | Type and number of substituent groups per CD molecule | ST-246 lot # | ST-246 solubility (mg/mL) at 37° C. CD concentration | | |
|---|---|---|---|---|---|
| | | | 20% | 32% | 40% |
| Cavitron ® W7 HP5 (ISP) | 4.1 to 5.1 HP-βCD | SG-08HO5M | 3.2 | 7.4 | 11.0 |
| | | SG-08HO6M | 3.3 | 7.3 | 11.5 |
| | | SG-08KO7M | 3.1 | 7.4 | 11.0 |
| Cavitron ® W7 HP7 (ISP) | 6.0 to 8.0 HP-βCD | SG-08HO5M | 1.6 | 4.5 | 7.4 |
| | | SG-08HO6M | 1.6 | 4.5 | 7.5 |
| | | SG-08KO7M | 1.5 | 4.4 | 7.4 |
| Captisol ® (CyDex) | 7 SBECD | SG-08HO5M | — | 1.0 | 1.6 |
| | | SG-08HO6M | — | 1.0 | 1.5 |
| | | SG-08HO7M | — | 1.0 | 1.5 |

Figure 5:
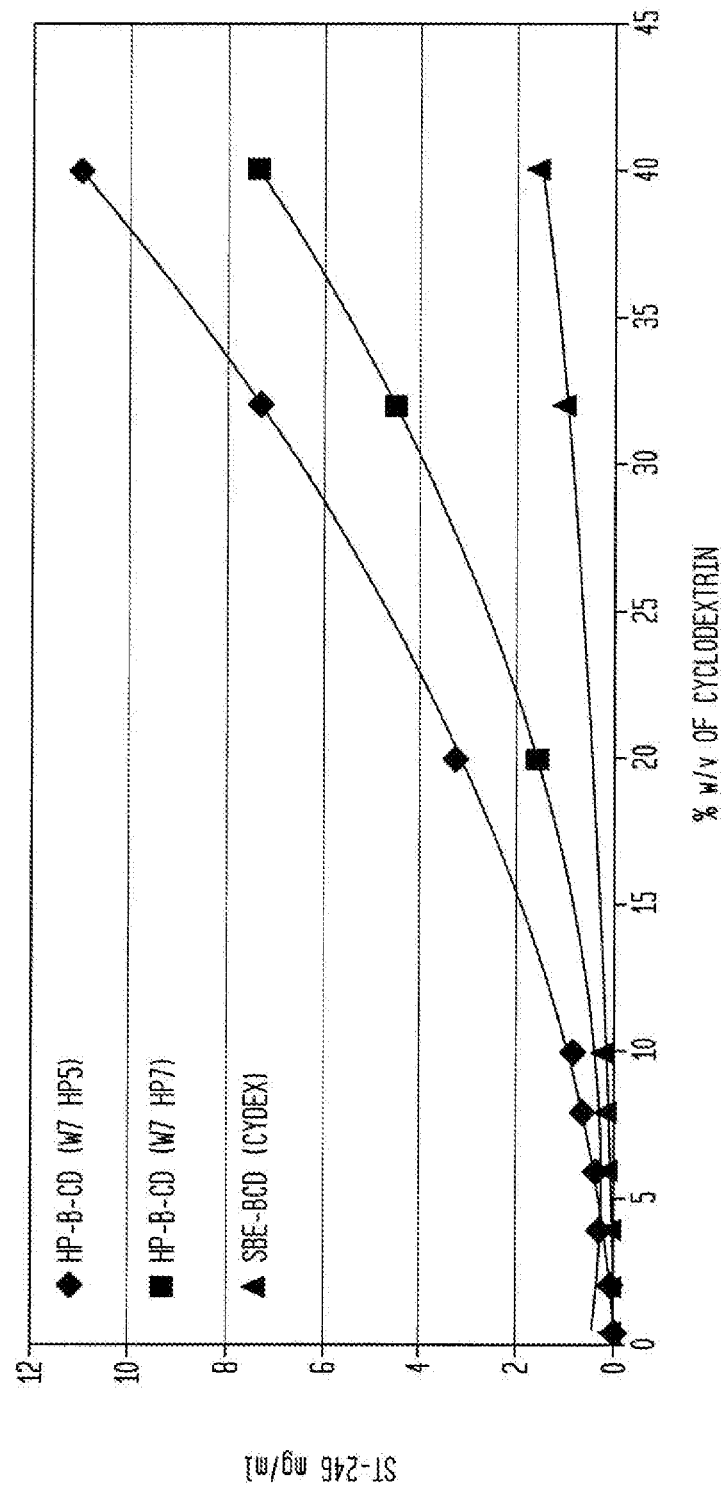
FIG. 5 depicts ST-246 aqueous solution of HP-ß-CD at 25° C.
Figure 6:
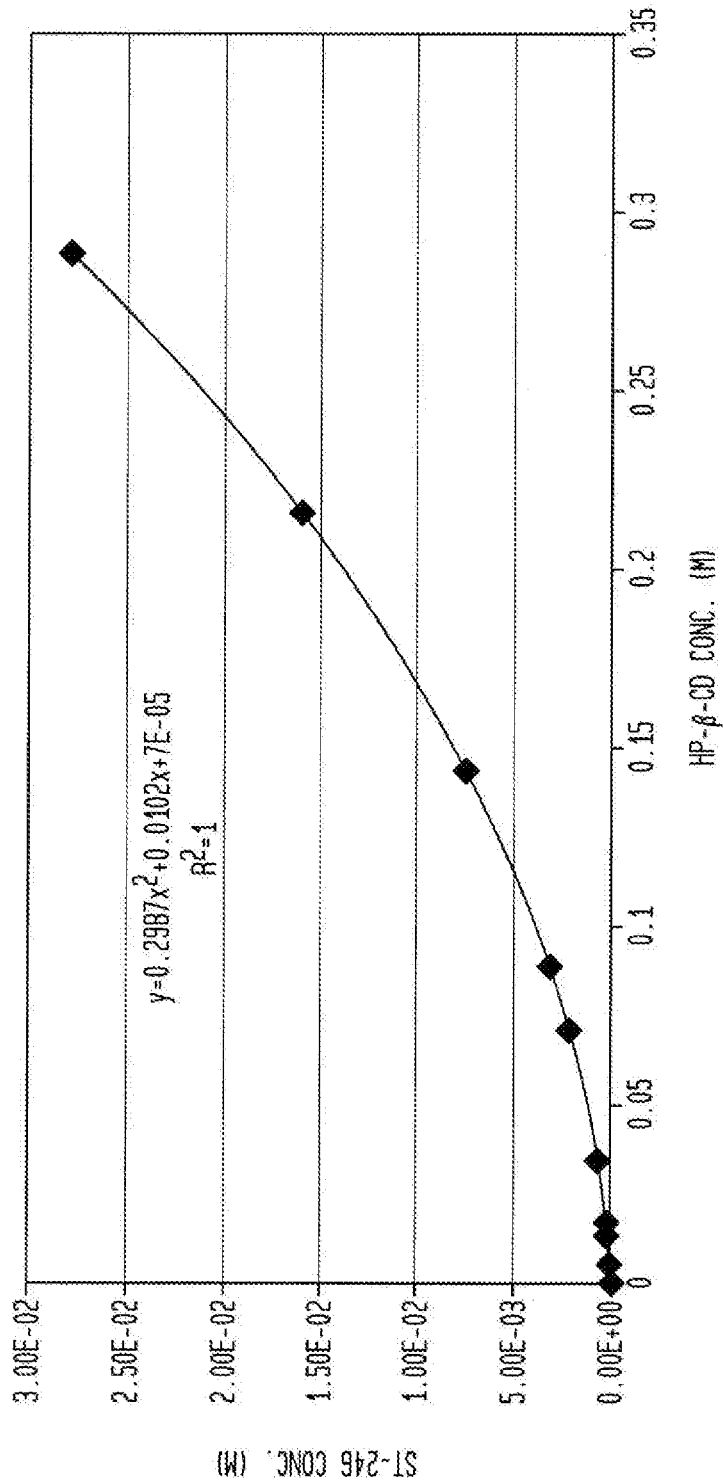
FIG. 6 depicts concentration of ST-246 as a function of HP-ß-CD at 25° C.

Further, FIG. 5 summarizes solubility of ST-246 as a function of cyclodextrin concentration. As shown in FIG. 5, the solubility of ST-246 increases with increased HP-ß-CD concentration. Further, HP-ß-CD provided for higher ST-246 solubility as compared to SBECD. Thus, data obtained from the solubilization experiments demonstrated that the highest ST-246 solubilization efficiency was achieved by both SBECD and HP-ß-CD, whereas HP-ß-CD outperforms the SBECD in terms of ST-246 solubilization efficiency.

Further studies were performed to determine the solubility of ST-246 in varying concentration of HP-β-CD at room temperature. For these experiments, the contents of the vials were brought to solubility equilibrium at a constant temperature of 25° C. while mixing the contents of the vial on a roto-mixer. Further, following 72 hours of mixing, the contents of the vial were filtered and the resulting filtrate was analyzed for the concentration of ST-246 using RP-HPLC. The concentrations of HP-β-CD used for the study are listed in Table 9. Further, the solubility of ST-246 by varying the concentration of HP-β-CD following HPLC analysis are listed in Table 9.

TABLE 9

Solubility of ST-246 as a function of HP-β-CD concentration at 25° C. following 72 hours shaking

| HP-β-CD (% w/v) | ST-246 (mg/mL) | HP-β-CD (mM) | ST-246 (mM) | HP-β-CD (M) | ST-246 (M) |
|---|---|---|---|---|---|
| 0 | 0.01 | 0.0 | 0.04 | 0.00 | 3.9E−05 |
| 0.1 | 0.02 | 0.7 | 0.05 | 0.001 | 4.6E−05 |
| 0.5 | 0.04 | 3.6 | 0.11 | 0.004 | 1.1E−04 |
| 1 | 0.07 | 7.2 | 0.17 | 0.007 | 1.7E−04 |
| 2 | 0.13 | 14.4 | 0.33 | 0.01 | 3.3E−04 |
| 2.5 | 0.15 | 18.0 | 0.37 | 0.02 | 3.7E−04 |

TABLE 9-continued

Solubility of ST-246 as a function of HP-β-CD concentration at 25° C. following 72 hours shaking

| HP-β-CD (% w/v) | ST-246 (mg/mL) | HP-β-CD (mM) | ST-246 (mM) | HP-β-CD (M) | ST-246 (M) |
|---|---|---|---|---|---|
| 5 | 0.32 | 35.9 | 0.81 | 0.04 | 8.1E−04 |
| 10 | 0.9 | 71.9 | 2.28 | 0.07 | 2.3E−03 |
| 12.5 | 1.35 | 89.8 | 3.42 | 0.09 | 3.4E−03 |
| 20 | 3.07 | 143.8 | 7.79 | 0.14 | 7.8E−03 |
| 30 | 6.33 | 215.6 | 16.05 | 0.22 | 1.6E−02 |
| 40 | 10.93 | 287.5 | 27.72 | 0.29 | 2.8E−02 |

Figure 7:
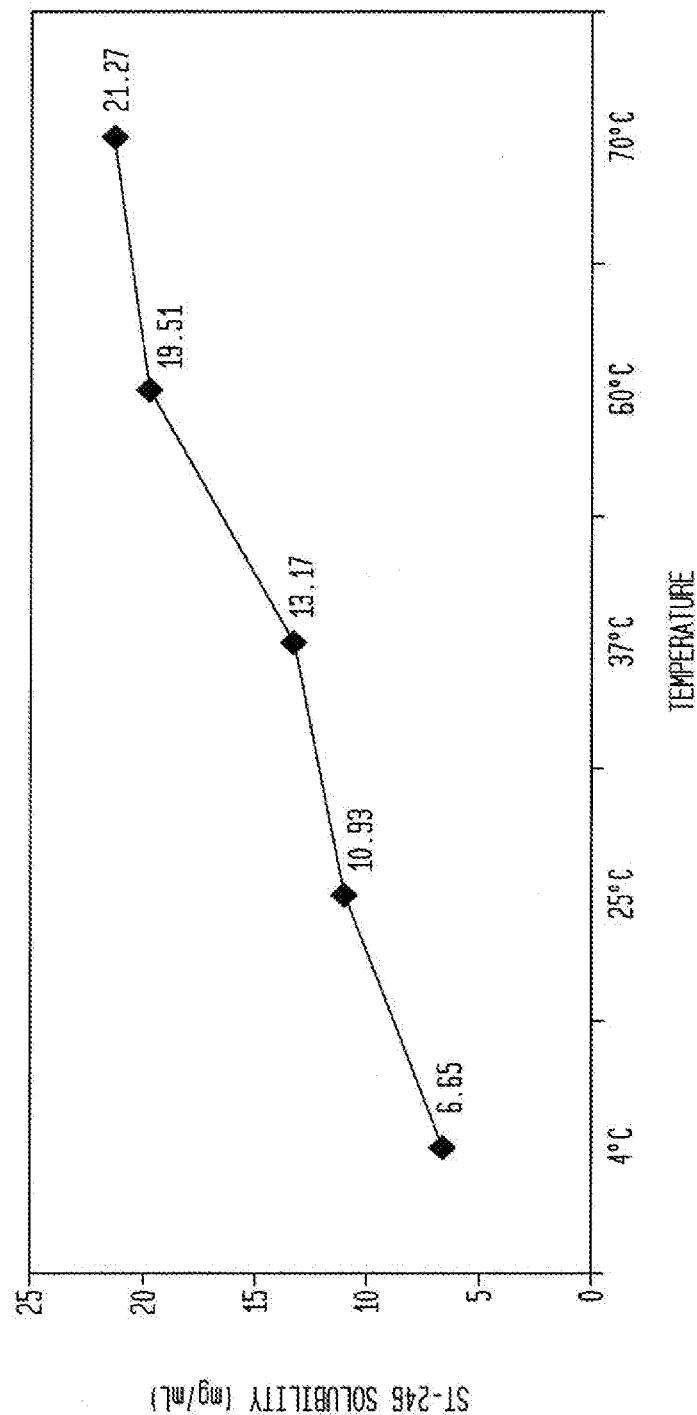
FIG. 7 depicts ST-246 solubility as a function of HP-ß-CD concentration.

The next series of experiments were done to determine solubility of ST-246 in 40% w/v HP-ß-CD composition as a function of temperature. These experiments determined that the concentration of ST-246 in composition increased with increasing temperature. As summarized in FIG. 7, a maximum solubility of 21.23 mg/mL was obtained with a 40% w/v HP-β-CD concentration at 70° C.

Figure 8:
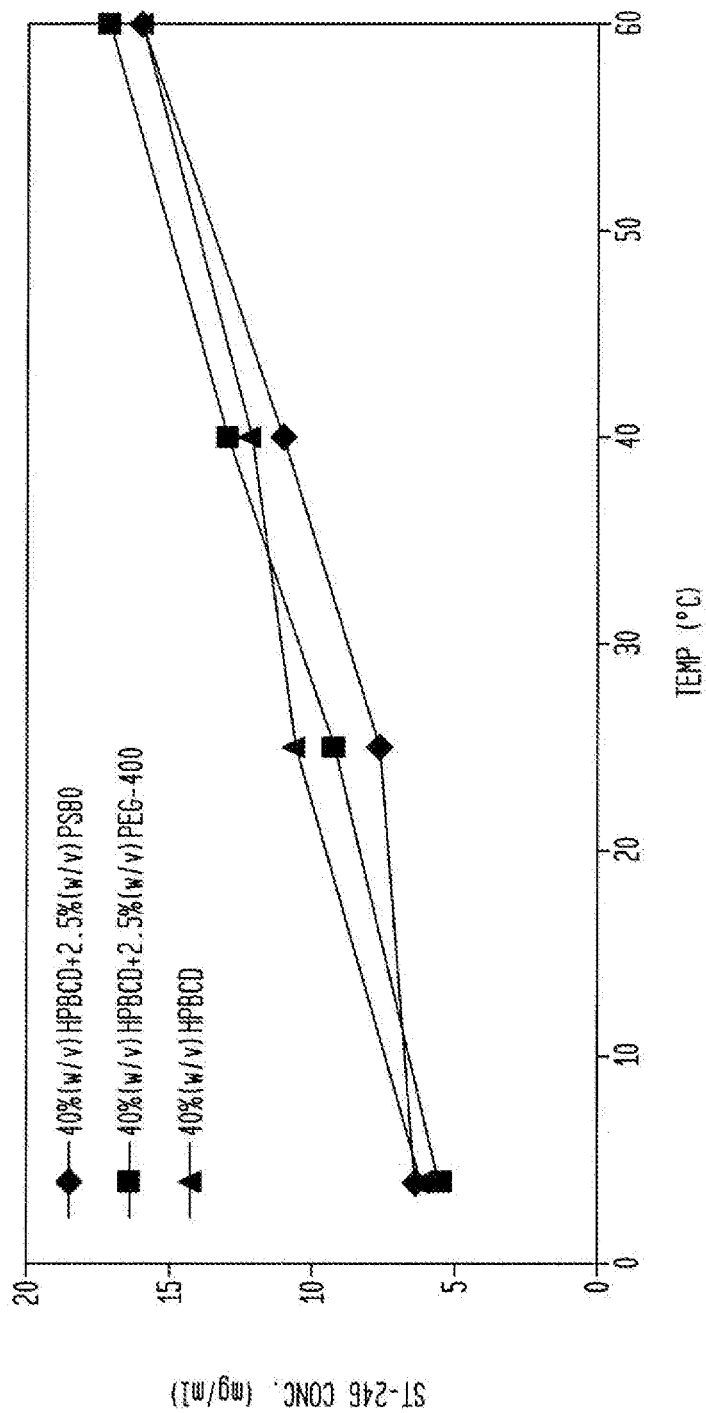
FIG. 8 depicts solubility of ST-246 in the presence of co-solvents as function of varying temperature.

The next series of experiments investigated the solubility of ST-246 in HP-ß-CD composition in presence of co-solvents/surfactants. The results of these experiments are summarized in Table 10 and FIG. 8. As evident from the results of the experiments, presence of cosolvents/surfactant can improve solution properties of drug in HP-ß-CD upon dilution and also helps dissolve drug much faster in HP-ß-CD.

TABLE 10

Solubility of ST-246 in the presence of cosolvents at various temperatures

| Temperature (° C.) | 40% (w/v) HPBCD + 2.5% (w/v) tween 80 | 40% (w/v) HPBCD + 2.5% (w/v) PEG-400 | 40% (w/v) HPBCD |
|---|---|---|---|
| 4 | 6.29 | 5.47 | 6.05 |
| 25 | 7.57 | 9.21 | 10.59 |
| 40 | 11.16 | 12.99 | 12.23 |
| 60 | 16.24 | 17.41 | 16.21 |

Solubility data presented in Table 10 suggest that presence of cosolvent (PEG 400) or non-ionic surfactant (tween 80) does not improve ST-246 solubility in HP-ß-CD and hence no further work was done to evaluate ternary complexation.

Further series of experiments were carried out to identify a pH range for maximum solubility of ST-246 in HPBCD composition. For these experiments, various composition of ST-246 in 40% HPBCD was prepared with pH ranging from 4.0 to 10.5. The composition was prepared at 25° C. and 2° C.-8° C. The following table consists of the composition studied and the buffer evaluated in the pH range of 4.0 through 10.5. The results of these experiments are summarized in Table 11.

TABLE 11

Compositions of formulations tested for the effect of pH on solubility of ST-246

| Sample # | Kleptose HP-β-CD (% w/v) | pH | Buffer |
|---|---|---|---|
| ST246-027-1 | 40 | 4.0 | 50 mM Citrate/Phosphate |
| ST246-027-2 |  | 4.5 |  |
| ST246-027-3 |  | 5.0 |  |
| ST246-027-4 |  | 5.5 |  |
| ST246-027-5 |  | 6.0 | 50 mM Phosphate |
| ST246-027-6 |  | 6.5 |  |
| ST246-027-7 |  | 7.0 |  |
| ST246-027-8 |  | 7.5 |  |
| ST246-027-9 |  | 8.0 |  |
| ST246-027-10 |  | 9.0 | 50 mM Glycine |
| ST246-027-11 |  | 9.5 |  |
| ST246-027-12 |  | 10.0 |  |
| ST246-027-13 |  | 10.5 |  |

For these experiments, an excess of ST-246 was added to vials containing 5 mL of the pH buffered HP-ß-CD solutions. The samples vials were rotomixed for more than 72 hours at 2-8° C. and 25° C. Samples were filtered using a 0.2 um PVDF membrane filter and the filtrate was diluted appropriately and analyzed for ST-246 content using RP-HPLC. Further, the pH of the samples was monitored before and after the solubility study was initiated. pH measurements indicated that there were no significant changes before and after the samples have reached equilibrium. The solubility of ST-246 achieved in 40% HPBCD composition as a function of varying pH is depicted in FIG. 9.

Figure 9:
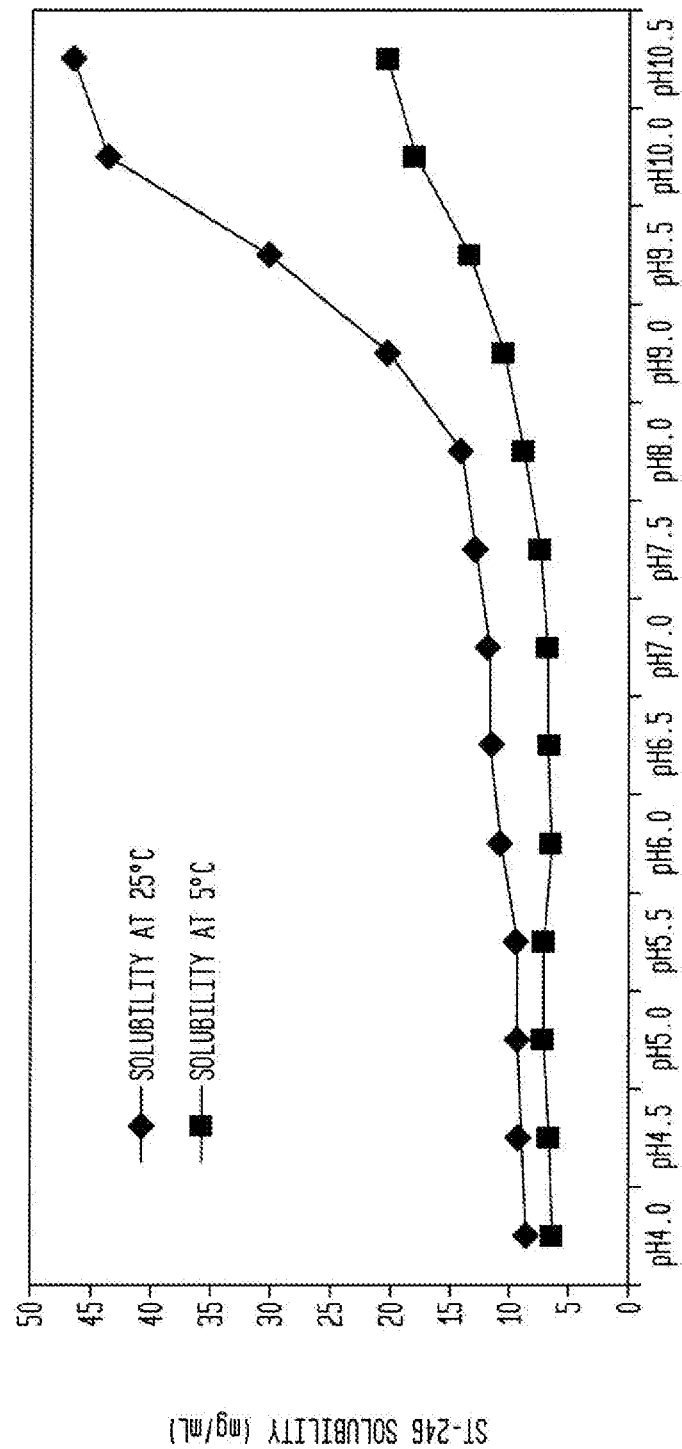
FIG. 9 depicts effect of pH on the solubility of ST-246 at 25° C. and 5° C.
Figure 10:
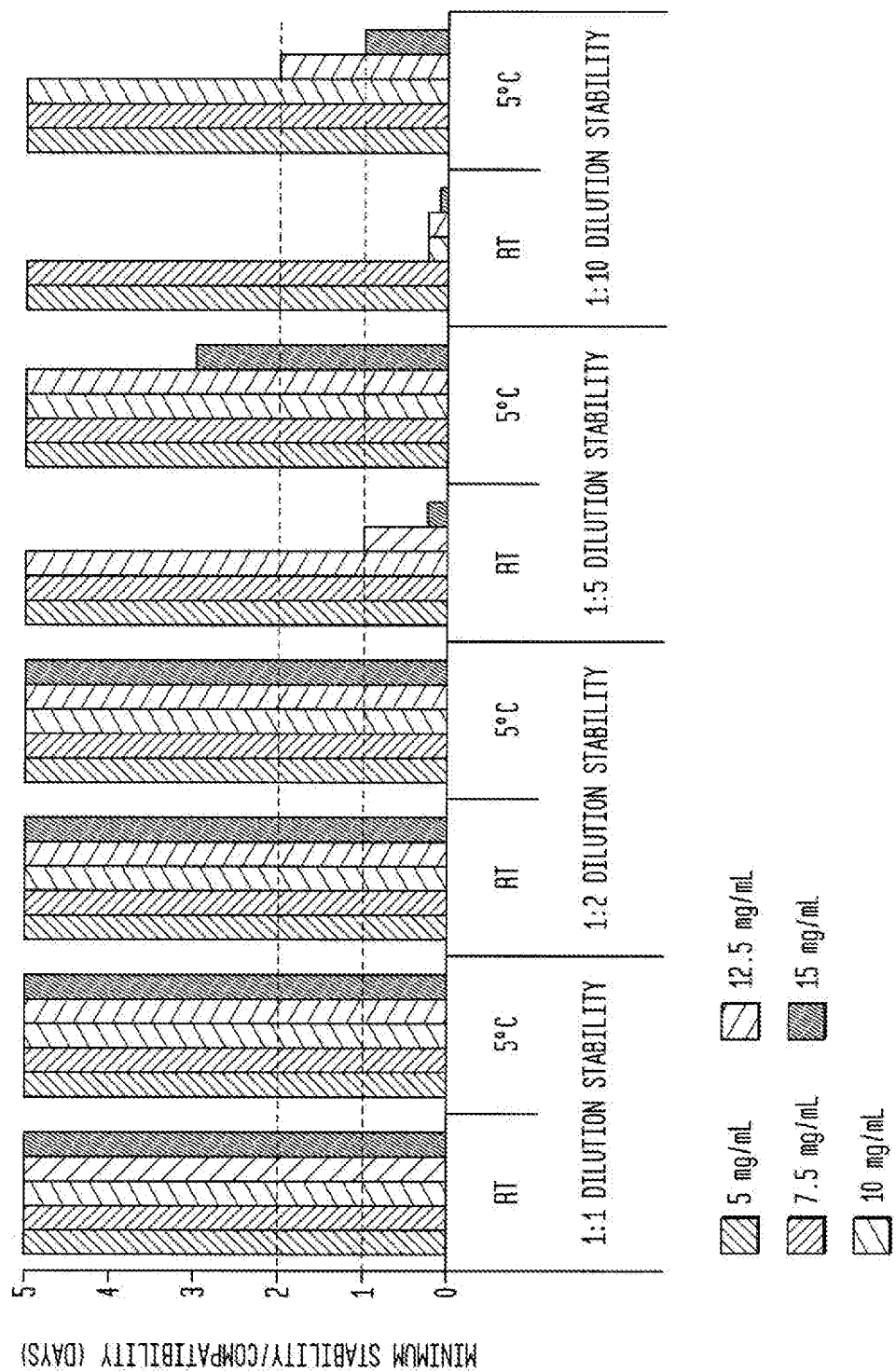
FIG. 10 depicts effect of dilution stability of intravenous formulations containing HP-ß-CD.

As shown in FIG. 9, an increase in solubility was observed with an increase in pH from 4.0 to 10.5 at both 2° C.-8° C. and 25° C. For the next series of experiments, scale-up studies of injectable ST-246 (have been initiated to understand the effect of batch size on complexation of ST-246 with HP-ß-CD. For these experiments, formulations have been prepared using parenteral grade HP-ß-CD. Samples from these studies have been placed on stability at cold storage temperature (2° C. to 8° C.), controlled room temperature (25° C.) and warm temperature (40° C.). At regular time intervals samples are removed, observed for any physical changes (precipitation, color change, etc.) and assayed for purity using HPLC to detect any degradation of ST-246.

ST-246, Form I, II, III, IV, V and VI were formulated for liquid administration. Suitable dosage forms comprises ST-246 ranging from about 2 mg/ml to about 20 mg/ml and HPBCD, ranging from about 12.5 mg/ml to about 40 mg/ml. Optionally, the formulations further comprises mannitol, trehalose dehydrate, lactose monohydrate, and purified water such that the total volume of the liquid formulation is about 100 ml. For these formulations, the pH may be adjusted and maintained form 2.5 to 6.0, by using HCL/NaOH, citric acid/Na citrate buffer, and other buffers including but not limited to acetate, tartarate, glycine, glucoronic acid. The above described liquid formulations are summarized in Tables 12-16.

TABLE 12

Examples of compositions of 5 mg/mL ST-246 IV formulations

| Ingredient | Composition # | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| | Quantity for 100 mL (g) | | | | | | | | | | | |
| ST-246 | 0.5 | 0.5 | 0.5 | 0.5 | 0.5 | 0.5 | 0.5 | 0.5 | 0.5 | 0.5 | 0.5 | 0.5 |
| HPBCD | 40 | 40 | 40 | 40 | 40 | 40 | 40 | 40 | 40 | 40 | 40 | 40 |
| Mannitol | — | — | — | 1 | 1 | 1 | — | — | — | — | — | — |
| Trehalose Dihydrate | — | — | — | — | — | — | 1 | 1 | 1 | — | — | — |
| Lactose Monohydrate | — | — | — | — | — | — | — | — | — | 1 | 1 | 1 |
| pH adjusted to 3.0 to 5.0 using 0.1N HCl/NaOH | — | q.s. | — | — | q.s. | — | — | q.s. | — | — | q.s. | — |
| pH adjusted to 3.0 to 5.0 using citrate buffer | — | — | q.s. | — | — | q.s. | — | — | q.s. | — | — | q.s. |
| Purified water Q.S. (mL) | 100 | 100 | 100 | 100 | 100 | 100 | 100 | 100 | 100 | 100 | 100 | 100 |

TABLE 13

Examples of compositions of 10 mg/mL ST-246 IV formulations

| Ingredient | Composition # | | | | | | | | | | | |
|---|---|---|---|---|---|---|---|---|---|---|---|---|
| | 13 | 14 | 15 | 16 | 17 | 18 | 19 | 20 | 21 | 22 | 23 | 24 |
| | Quantity for 100 mL (g) | | | | | | | | | | | |
| ST-246 | 0.75 | 0.75 | 0.75 | 0.75 | 0.75 | 0.75 | 0.75 | 0.75 | 0.75 | 0.75 | 0.75 | 0.75 |
| HPBCD | 40 | 40 | 40 | 40 | 40 | 40 | 40 | 40 | 40 | 40 | 40 | 40 |
| Mannitol | — | — | — | 1 | 1 | 1 | — | — | — | — | — | — |
| Trehalose Dihydrate | — | — | — | — | — | — | 1 | 1 | 1 | — | — | — |
| Lactose Monohydrate | — | — | — | — | — | — | — | — | — | 1 | 1 | 1 |
| pH adjusted to 3.0 to 5.0 using 0.1N HCl/NaOH | — | q.s. | — | — | q.s. | — | — | q.s. | — | — | q.s. | — |
| pH adjusted to 3.0 to 5.0 using citrate buffer | — | — | q.s. | — | — | q.s. | — | — | q.s. | — | — | q.s. |
| Purified water Q.S. (mL) | 100 | 100 | 100 | 100 | 100 | 100 | 100 | 100 | 100 | 100 | 100 | 100 |

TABLE 14

Examples of compositions of 12.5 mg/mL ST-246 IV formulations

| Ingredient | Composition # | | | | | | | | | | | |
|---|---|---|---|---|---|---|---|---|---|---|---|---|
| | 25 | 26 | 27 | 28 | 29 | 30 | 31 | 32 | 33 | 34 | 35 | 36 |
| | Quantity for 100 mL (g) | | | | | | | | | | | |
| ST-246 | 1 | 1 | 1 | 1 | 1 | 1 | 1 | 1 | 1 | 1 | 1 | 1 |
| HPBCD | 40 | 40 | 40 | 40 | 40 | 40 | 40 | 40 | 40 | 40 | 40 | 40 |
| Mannitol | — | — | — | 1 | 1 | 1 | — | — | — | — | — | — |
| Trehalose Dihydrate | — | — | — | — | — | — | 1 | 1 | 1 | — | — | — |
| Lactose Monohydrate | — | — | — | — | — | — | — | — | — | 1 | 1 | 1 |
| pH adjusted to 3.0 to 5.0 using 0.1N HCl/NaOH | — | q.s. | — | — | q.s. | — | — | q.s. | — | — | q.s. | — |
| pH adjusted to 3.0 to 5.0 using citrate buffer | — | — | q.s. | — | — | q.s. | — | — | q.s. | — | — | q.s. |
| Purified water Q.S. (mL) | 100 | 100 | 100 | 100 | 100 | 100 | 100 | 100 | 100 | 100 | 100 | 100 |

TABLE 15

Examples of compositions of 15 mg/mL ST-246 IV formulations

| Ingredient | Composition # | | | | | | | | | | | |
|---|---|---|---|---|---|---|---|---|---|---|---|---|
| | 37 | 38 | 39 | 40 | 41 | 42 | 43 | 44 | 45 | 46 | 47 | 48 |
| | Quantity for 100 mL (g) | | | | | | | | | | | |
| ST-246 | 1.5 | 1.5 | 1.5 | 1.5 | 1.5 | 1.5 | 1.5 | 1.5 | 1.5 | 1.5 | 1.5 | 1.5 |
| HPBCD | 40 | 40 | 40 | 40 | 40 | 40 | 40 | 40 | 40 | 40 | 40 | 40 |
| Mannitol | — | — | — | 1 | 1 | 1 | — | — | — | — | — | — |
| Trehalose Dihydrate | — | — | — | — | — | — | 1 | 1 | 1 | — | — | — |
| Lactose Monohydrate | — | — | — | — | — | — | — | — | — | 1 | 1 | 1 |
| pH adjusted to 3.0 to 5.0 using 0.1N HCl/NaOH | — | q.s. | — | — | q.s. | — | — | q.s. | — | — | q.s. | — |
| pH adjusted to 3.0 to 5.0 using citrate buffer | — | — | q.s. | — | — | q.s. | — | — | q.s. | — | — | q.s. |
| Purified water Q.S. (mL) | 100 | 100 | 100 | 100 | 100 | 100 | 100 | 100 | 100 | 100 | 100 | 100 |

TABLE 16

Examples of compositions of 20 mg/mL ST-246 IV formulations

| Ingredient | Composition # | | | | | | | | | | | |
|---|---|---|---|---|---|---|---|---|---|---|---|---|
| | 49 | 50 | 51 | 52 | 53 | 54 | 55 | 56 | 57 | 58 | 59 | 60 |
| | Quantity for 100 mL (g) | | | | | | | | | | | |
| ST-246 | 2 | 2 | 2 | 2 | 2 | 2 | 2 | 2 | 2 | 2 | 2 | 2 |
| HPBCD | 40 | 40 | 40 | 40 | 40 | 40 | 40 | 40 | 40 | 40 | 40 | 40 |
| Mannitol | — | — | — | 1 | 1 | 1 | — | — | — | — | — | — |
| Trehalose Dihydrate | — | — | — | — | — | — | 1 | 1 | 1 | — | — | — |
| Lactose Monohydrate | — | — | — | — | — | — | — | — | — | 1 | 1 | 1 |
| pH adjusted to 3.0 to 5.0 using 0.1N HCl/NaOH | — | q.s. | — | — | q.s. | — | — | q.s. | — | — | q.s. | — |
| pH adjusted to 3.0 to 5.0 using citrate buffer | — | — | q.s. | — | — | q.s. | — | — | q.s. | — | — | q.s. |
| Purified water Q.S. (mL) | 100 | 100 | 100 | 100 | 100 | 100 | 100 | 100 | 100 | 100 | 100 | 100 |

Further liquid formulations comprising ST-246, Form I, II, III, IV, V and VI are summarized in Tables 17-21. Suitable dosage forms comprises ST-246 ranging from about 2 mg/ml to about 20 mg/ml and HPBCD, ranging from about 12.5 mg/ml to about 40 mg/ml. Optionally, the formulations further comprise polyethylene glycol 400, polysorbate 80, polyethylene glycol 300, and purified water up to 100 ml. For these formulations, the pH may be adjusted and maintained form 2.5 to 6.0, by using HCL/NaOH, citric acid/Na citrate buffer, and other buffers including but not limited to acetate, tartarate, glycine, glucoronic acid.

TABLE 17

Examples of compositions of 5 mg/mL ST-246 IV formulations containing cosolvents/surfactants

| Ingredient | Composition # | | | | | | | | | | | |
|---|---|---|---|---|---|---|---|---|---|---|---|---|
| | 61 | 62 | 63 | 64 | 65 | 66 | 67 | 68 | 69 | 70 | 71 | 72 |
| | Quantity for 100 mL (g) | | | | | | | | | | | |
| ST-246 | 0.5 | 0.5 | 0.5 | 0.5 | 0.5 | 0.5 | 0.5 | 0.5 | 0.5 | 0.5 | 0.5 | 0.5 |
| HPBCD | 40 | 40 | 40 | 40 | 40 | 40 | 40 | 40 | 40 | 40 | 40 | 40 |
| Polyethylene Glycol 400 | 1 | 1 | 1 | 1 | 1 | 1 | — | — | — | — | — | — |
| Polysorbate 80 | — | — | — | 1 | 1 | 1 | 1 | 1 | 1 | — | — | — |
| Polyethylene Glycol 300 | — | — | — | — | — | — | 1 | 1 | 1 | 1 | 1 | 1 |
| pH adjusted to 3.0 to 5.0 using 0.1N HCl/NaOH | — | q.s. | — | — | q.s. | — | — | q.s. | — | — | q.s. | — |
| pH adjusted to 3.0 to 5.0 using citrate buffer | — | — | q.s. | — | — | q.s. | — | — | q.s. | — | — | q.s. |
| Purified water Q.S. (mL) | 100 | 100 | 100 | 100 | 100 | 100 | 100 | 100 | 100 | 100 | 100 | 100 |

TABLE 18

Compositions of 7.5 mg/mL ST-246 IV formulations containing co-solvents

| Ingredient | 73 | 74 | 75 | 76 | 77 | 78 | 79 | 80 | 81 | 82 | 83 | 84 |
|---|---|---|---|---|---|---|---|---|---|---|---|---|
| | \multicolumn{12}{c}{Quantity for 100 mL (g)} | | | | | | | | | | | |
| ST-246 | 0.75 | 0.75 | 0.75 | 0.75 | 0.75 | 0.75 | 0.75 | 0.75 | 0.75 | 0.75 | 0.75 | 0.75 |
| HPBCD | 40 | 40 | 40 | 40 | 40 | 40 | 40 | 40 | 40 | 40 | 40 | 40 |
| Polyethylene Glycol 400 | 1 | 1 | 1 | 1 | 1 | 1 | — | — | — | — | — | — |
| Polysorbate 80 | — | — | — | 1 | 1 | 1 | 1 | 1 | 1 | — | — | — |
| Polyethylene Glycol 300 | — | — | — | — | — | — | 1 | 1 | 1 | 1 | 1 | 1 |
| pH adjusted to 3.0 to 5.0 using 0.1N HCl/NaOH | — | q.s. | — | — | q.s. | — | — | q.s. | — | — | q.s. | — |
| pH adjusted to 3.0 to 5.0 using citrate buffer | — | — | q.s. | — | — | q.s. | — | — | q.s. | — | — | q.s. |
| Purified water Q.S. (mL) | 100 | 100 | 100 | 100 | 100 | 100 | 100 | 100 | 100 | 100 | 100 | 100 |

TABLE 19

Compositions of 10 mg/mL ST-246 IV formulations containing co-solvents

| Ingredient | 85 | 86 | 87 | 88 | 89 | 90 | 91 | 92 | 93 | 94 | 95 | 96 |
|---|---|---|---|---|---|---|---|---|---|---|---|---|
| | \multicolumn{12}{c}{Quantity for 100 mL (g)} | | | | | | | | | | | |
| ST-246 | 1 | 1 | 1 | 1 | 1 | 1 | 1 | 1 | 1 | 1 | 1 | 1 |
| HPBCD | 40 | 40 | 40 | 40 | 40 | 40 | 40 | 40 | 40 | 40 | 40 | 40 |
| Polyethylene Glycol 400 | 1 | 1 | 1 | 1 | 1 | 1 | — | — | — | — | — | — |
| Polysorbate 80 | — | — | — | 1 | 1 | 1 | 1 | 1 | 1 | — | — | — |
| Polyethylene Glycol 300 | — | — | — | — | — | — | 1 | 1 | 1 | 1 | 1 | 1 |
| pH adjusted to 3.0 to 5.0 using 0.1N HCl/NaOH | — | q.s. | — | — | q.s. | — | — | q.s. | — | — | q.s. | — |
| pH adjusted to 3.0 to 5.0 using citrate buffer | — | — | q.s. | — | — | q.s. | — | — | q.s. | — | — | q.s. |
| Purified water Q.S. (mL) | 100 | 100 | 100 | 100 | 100 | 100 | 100 | 100 | 100 | 100 | 100 | 100 |

TABLE 20

Compositions of 15 mg/mL ST-246 IV formulations containing co-solvents

| Ingredient | 97 | 98 | 99 | 100 | 101 | 102 | 103 | 104 | 105 | 106 | 107 | 108 |
|---|---|---|---|---|---|---|---|---|---|---|---|---|
| | \multicolumn{12}{c}{Quantity for 100 mL (g)} | | | | | | | | | | | |
| ST-246 | 1.5 | 1.5 | 1.5 | 1.5 | 1.5 | 1.5 | 1.5 | 1.5 | 1.5 | 1.5 | 1.5 | 1.5 |
| HPBCD | 40 | 40 | 40 | 40 | 40 | 40 | 40 | 40 | 40 | 40 | 40 | 40 |
| Polyethylene Glycol 400 | 1 | 1 | 1 | 1 | 1 | 1 | — | — | — | — | — | — |
| Polysorbate 80 | — | — | — | 1 | 1 | 1 | 1 | 1 | 1 | — | — | — |
| Polyethylene Glycol 300 | — | — | — | — | — | — | 1 | 1 | 1 | 1 | 1 | 1 |
| pH adjusted to 3.0 to 5.0 using 0.1N HCl/NaOH | — | q.s. | — | — | q.s. | — | — | q.s. | — | — | q.s. | — |
| pH adjusted to 3.0 to 5.0 using citrate buffer | — | — | q.s. | — | — | q.s. | — | — | q.s. | — | — | q.s. |
| Purified water Q.S. (mL) | 100 | 100 | 100 | 100 | 100 | 100 | 100 | 100 | 100 | 100 | 100 | 100 |

TABLE 21

Compositions of 20 mg/mL ST-246 IV formulations containing co-solvents

| Ingredient | Composition # |  |  |  |  |  |  |  |  |  |  |  |
|---|---|---|---|---|---|---|---|---|---|---|---|---|
|  | 109 | 110 | 111 | 112 | 113 | 114 | 115 | 116 | 117 | 118 | 119 | 120 |
|  | Quantity for 100 mL (g) |  |  |  |  |  |  |  |  |  |  |  |
| ST-246 | 2 | 2 | 2 | 2 | 2 | 2 | 2 | 2 | 2 | 2 | 2 | 2 |
| HPBCD | 40 | 40 | 40 | 40 | 40 | 40 | 40 | 40 | 40 | 40 | 40 | 40 |
| Polyethylene Glycol 400 | 1 | 1 | 1 | 1 | 1 | 1 | — | — | — | — | — | — |
| Polysorbate 80 | — | — | — | 1 | 1 | 1 | 1 | 1 | 1 | — | — | — |
| Polyethylene Glycol 300 | — | — | — | — | — | — | 1 | 1 | 1 | 1 | 1 | 1 |
| pH adjusted to 3.0 to 5.0 using 0.1N HCl/NaOH | — | q.s. | — | — | q.s. | — | — | q.s. | — | — | q.s. | — |
| pH adjusted to 3.0 to 5.0 using citrate buffer | — | — | q.s. | — | — | q.s. | — | — | q.s. | — | — | q.s. |
| Purified water Q.S. (mL) | 100 | 100 | 100 | 100 | 100 | 100 | 100 | 100 | 100 | 100 | 100 | 100 |

Further, Table 22 summarizes ranges for ST-246 and HPBCD in various formulations.

TABLE 22

Compositions of ST-246 IV formulations by varying the HPBCD concentrations

| Ingredient | Composition # |  |  |  |  |  |
|---|---|---|---|---|---|---|
|  | 121 | 122 | 123 | 124 | 125 | 126 |
|  | Quantity for 100 mL (g) |  |  |  |  |  |
| ST-246 | 2 | 2 | 2 | 5 | 10 | 20 |
| HPBCD | 12.5 | 20 | 30 | 40 | 40 | 40 |
| Purified water Q.S. (mL) | 100 | 100 | 100 | 100 | 100 | 100 |

Further, for these experiments, the compatibility of ST-246 prototype formulations with 0.9% (w/v) NaCl, a commonly used infusion fluid, was evaluated. Five formulations of ST-246 were prepared at various concentrations using 40% (w/v) HP-ß-CD. The formulations were diluted with 0.9% (w/v) NaCl in the ratios of 1:1, 1:2, 1:5 and 1:10. The diluted solutions were stored at RT and 5° C. and were monitored for their physical stability by visual inspection, microscopy and per USP guideliens at regular time intervals. The results of these experiments are summarized in Table 23.

TABLE 23

Stability and Compatibility of ST-246 IV Formulations Following Dilution

| ST-246 (mg/mL) | Stability/Compatibility following dilution |
|---|---|
| 5 | More than 48 hours at all dilutions when stored at RT or 5° C. |
| 7.5 | More than 48 hours at all dilutions when stored at RT or 5° C. |
| 10 | More than 48 hours at 1:1, 1:2 and 1:5 dilutions when stored at RT or 5° C. |
| 12.5 | more than 48 hours at 1:1 and 1:2 when stored at RT or 5° C. More than 48 hours at 1:5 dilution when stored at 5° C. More than 24 hours at 1:5 dilution when stored at RT |
| 15 | More than 48 hours at 1:1 and 1:2 when stored at RT or 5° C. More than 48 hours at 1:5 dilution when stored at 5° C. 24 hours at 1:10 dilution when stored at 5° C. |

Intravenous formulations of ST-246 at 5-20 mg/mL were found to be compatible with 0.9% NaCl for at least 48 hours at 1:2 dilution (expected dilution in clinical situation) when stored at RT and refrigerated conditions.

The results obtained indicate that solutions diluted 1:1 and 1:2 containing ST-246 concentrations ranging from 5-20 mg/mL were found to be compatible with 0.9% NaCl for at least 48 hours when stored at RT and refrigerated conditions.

Pharmacokinetics of ST-246 IV Formulations in Mouse, Rabbits and Non-Human Primates (NHP).

Intravenous (IV) administration of ST-246 formulation, comprising HPBCD, were evaluated in mice, rabbits and NHP. The resulting pharmacokinetic parameters have been compared with those obtained after oral administration. The results of these studies suggest that intravenous ST-246 formulations exhibit similar pharmacokinetic parameters as compared to oral ST-246 formulations when administered in subjects in need thereof. Furthermore the ST-246 formulations comprising HP-ß-CD appeared to be safe and the pharmacokinetic parameters were acceptable.

Pharmacokinetic (PK) Profile in Mouse:

Three preliminary mouse studies (ASM246, ASM250 and ASM257) unequivocally demonstrated that short infusions of ST-246 intravenous formulations provided exposure similar to that obtained after ST-246 oral dosing, but at much lower doses. Specifically, ten-minute ST-246 infusion at four doses (3, 10, 30 and 75 mg/kg) were evaluated in female CD-1 mice and the plasma concentrations were measured at the end of these infusions. Further, those concentrations were, as expected, the peak plasma concentrations and the average plasma concentration at the end of the 10-minute infusion of 75 mg/kg was 238, 333 ng/mL. Table 24 summarizes the $C_{max}$ (ng/mL) plasma concentrations and the $AUC_{0-24}$ (hr*ng/mL) for the ST-246 intravenous formulation and the pivotal oral formulation parameters.

TABLE 24

Comparison of $C_{max}$ and AUC Values

| Dose (mg/kg) | Formulation | Route | $C_{max}$ (ng/mL) M | $C_{max}$ (ng/mL) F | $AUC_{0-24}$ (hr*ng/mL) M | $AUC_{0-24}$ (hr*ng/mL) F | $C_{max}$ Ratio* IV/PO F | AUC Ratio* IV/PO F |
|---|---|---|---|---|---|---|---|---|
| | Study ASM246 | | | | | | | |
| 2.3 | 32% HPBCD | IV Bolus | 19977 | 22403 | 73327 | 87757 | 0.2 | 0.08 |
| 7.6 | | | 53834 | 37589 | 170100 | 218136 | 0.4 | 0.2 |
| 34.3 | | | 191174 | 162327 | 797725 | 873097 | 1.6 | 0.8 |
| | Study ASM250 | | | | | | | |
| 3 | 40% HPBCD | Slow IV Bolus | 78428* | | 100000* | | — | — |
| 30 | | (5-min) | 148918* | | 300000* | | — | — |
| | Study ASM257 | | | | | | | |
| 30 | 40% HPBCD | 5-min Infusion | ND | 120051 | — | — | 1.15 | — |
| 30 | | 10-min Infusion | ND | 126639 | — | — | 1.22 | — |
| | Study ASM260 | | | | | | | |
| 3 | 40% HPBCD | 10-min Infusion | ND | 16700 | ND | 67907 | 0.16 | 0.06 |
| 10 | | | ND | 63500 | ND | 407609 | 0.6 | 0.4 |
| 30 | | | ND | 147333 | ND | 709202 | 1.4 | 0.7 |
| 75 | | | ND | 238333 | ND | 1252858 | 2.3 | 1.2 |
| | Pivotal Oral Formulation Studies-Day 1 Values 246-TX-001 | | | | | | | |
| 30 | HPMC | PO (oral) | 30395 | 37502 | 241467 | 292094 | — | — |
| 100 | Suspension | | 38360 | 43798 | 342855 | 455830 | — | — |
| 300 | | | 48450 | 63976 | 484162 | 668735 | — | — |
| 1000 | | | 61076 | 66271 | 719348 | 851749 | — | — |
| | 246-TX-006 (28-Day Study) | | | | | | | |
| 500 | HPMC** | PO (oral) | 36648 | 56595 | 413416 | 515473 | — | — |
| 1000 | Suspension | | 49125 | 56561 | 416003 | 537466 | — | — |
| 2000 | | | 50933 | 69874 | 507951 | 607250 | — | — |
| | 2083-003-001-SN3 (3-Month Study) | | | | | | | |
| 300 | HPMC** | PO (oral) | 89400 | 89200 | 669961 | 688685 | — | — |
| 600 | Suspension | | 82800 | 95300 | 765268 | 853935 | — | — |
| 1000 | | | 94200 | 104000 | 1249135 | 1090088 | — | — |

*Value compared to highest value obtained from PO study-1000 mg/kg in 3-month study.

The results unequivocally demonstrate that ST-246 compositions comprising HP-ß-CD formulation are safe and effective and provide plasma concentration time profiles that closely mimicked those obtained after oral administration of ST-246.

PK profile in Rabbits: Intravenous ST-246 formulations comprising HP-ß-CD were administered to rabbits. Further, tolerability and pharmacokinetic parameters were evaluated after 5-minute slow IV push injections via the marginal ear vein in two male and two female naïve New Zealand White rabbits at doses of 3, 30, and 60 mg/kg ST-246.

As shown in Table 25, the peak plasma concentration using a 15-minute infusion at 3 mg/kg were 7225 ng/mL and 4345 ng/mL for male and female rabbits, respectively. In general the observed $C_{max}$ plasma concentrations and the AUC values were higher and the plasma elimination half-lives was longer for oral administration. The summary of the pharmacokinetic parameters in rabbits after oral and intravenous administration are shown in Table 25.

TABLE 25

Pharmacokinetic Parameters in Rabbits after PO and IV Doses

| Dose (mg/kg) | Formulation | Route | $C_{max}$ (ng/mL) M | $C_{max}$ (ng/mL) F | $AUC_{0-24}$ (hr*ng/mL) M | $AUC_{0-24}$ (hr*ng/mL) F | $T_{1/2}$ (hr) M | $T_{1/2}$ (hr) F |
|---|---|---|---|---|---|---|---|---|
| | 246-TX-012 | | | | | | | |
| 1 | PEG | IV | 769 | 679 | 1712 | 1150 | 1.1 | 0.69 |
| 100 | 1% HPMC E5/ 0.5% Tween80/ 97.5% H$_2$O | PO | 4480 | 1227 | 26396 | 8179 | 6 | 1.3 |
| | ASM253 | | | | | | | |
| 3 | 32% HPBCD | Slow IV | ª2720 | ª3335 | 1868 | 3214 | 3.2 | 3.2 |
| 30 | | Push (5 min) | 39950 | 37050 | 16220 | 14867 | 8.1 | 16.3 |
| 60 | | | 99850 | 88250 | 72327 | 60058 | 5.7 | 4.6 |

TABLE 25-continued

Pharmacokinetic Parameters in Rabbits after PO and IV Doses

| Dose (mg/kg) | Formulation | Route | $C_{max}$ (ng/mL) | $AUC_{0-24}$ (hr*ng/mL) | | | $T_{1/2}$ (hr) | |
|---|---|---|---|---|---|---|---|---|
| ASM258 | | | | | | | | |
| 3 | 32% HPBCD | Slow IV Push (15 min) | [b]7225 | [b]4345 | 3622 | 3154 | 1.7 | 0.7 |

[a]First sampling time at 5 minutes after End of Infusion
[b]First sampling time point at End of Infusion PK Profile in Cynomolgus Monkeys:

The study design included three groups of two male and two female monkeys. For these experiments, ST-246 was administered at 1, 3, and 10 mg/kg over a 4-hr intravenous infusion period by way of an implanted Vascular Access Port (VAP). For these experiments, the concentration of HP-ß-CD in the infusion fluid was 13.3% w/v. Plasma samples were collected pre-dose, and at 0.5, 1, and 2 hours after the start of the infusion as well as at the end of infusion (EOI) (4.0 hour±10 minutes), 0.25, 0.5, and 1 hour after the EOI and at 6, 8, 12, 16, 20, 24 and 48 hours after the start of the infusion to accurately determine the terminal elimination half-life.

The pharmacokinetic parameters ($C_{max}$ (ng/mL) plasma concentrations and the $AUC_{0-24}$ (hr*ng/mL)) in cynomolus monkeys at 1, 3 and 10 mg/Kg and the Oral formulation at 3, 10, 20 and 30 mg/kg over time are shown in the Table 26.

The four hour intravenous infusions of ST-246 was dose proportional and the plasma concentration time curves appeared to be biphasic with terminal elimination half-life values ranging from 6.6 hrs to 8.6 hours for the 1 to 10 mg/kg dose. The apparent volume of distribution (Vz as well as Vss) values did not change significantly over the dose range and neither did the clearance, which remained approximately 0.5 L/hr/kg over the dose range.

TABLE 26

IV ST-246 Study 246-TX-018 vs. Oral ST-246 Study 1151-065

| Dose mg/kg | HL_Lambda_z hr | $T_{max}$ hr | $C_{max}$ ng/mL | $AUC_{last}$ hr * ng/mL | $AUC_{INF\_obs}$ hr * ng/mL |
|---|---|---|---|---|---|
| 4 Hr-IV Infusion (246-TX-018) | | | | | |
| 1 | 6.6 ± 6.0 | 4.0 | 384 ± 112 | 1880 ± 455 | 1935 ± 459 |
| 3 | 8.5 ± 3.2 | 4.0 | 1053 ± 185 | 5652 ± 784 | 5828 ± 870 |
| 10 | 8.6 ± 1.3 | 4.0 | 4400 ± 935 | 21126 ± 3449 | 21273 ± 3395 |
| PO Administration (MPI 1151-065) | | | | | |
| 3 | 9.9 ± 6.0 | 3.3 | 496 ± 145 | 3863 ± 862 | 4527 ± 490 |
| 10 | 7.0 ± 0.9 | 3.8 | 1077 ± 279 | 10312 ± 3064 | 11802 ± 3669 |
| 20 | 7.2 ± 2.3 | 3.2 | 1475 ± 864 | 13389 ± 8018 | 15523 ± 9146 |
| 30 | 17.7 ± 13.8 | 3.6 | 1988 ± 873 | 20502 ± 8054 | 31901 ± 7362 |

Figure 11:
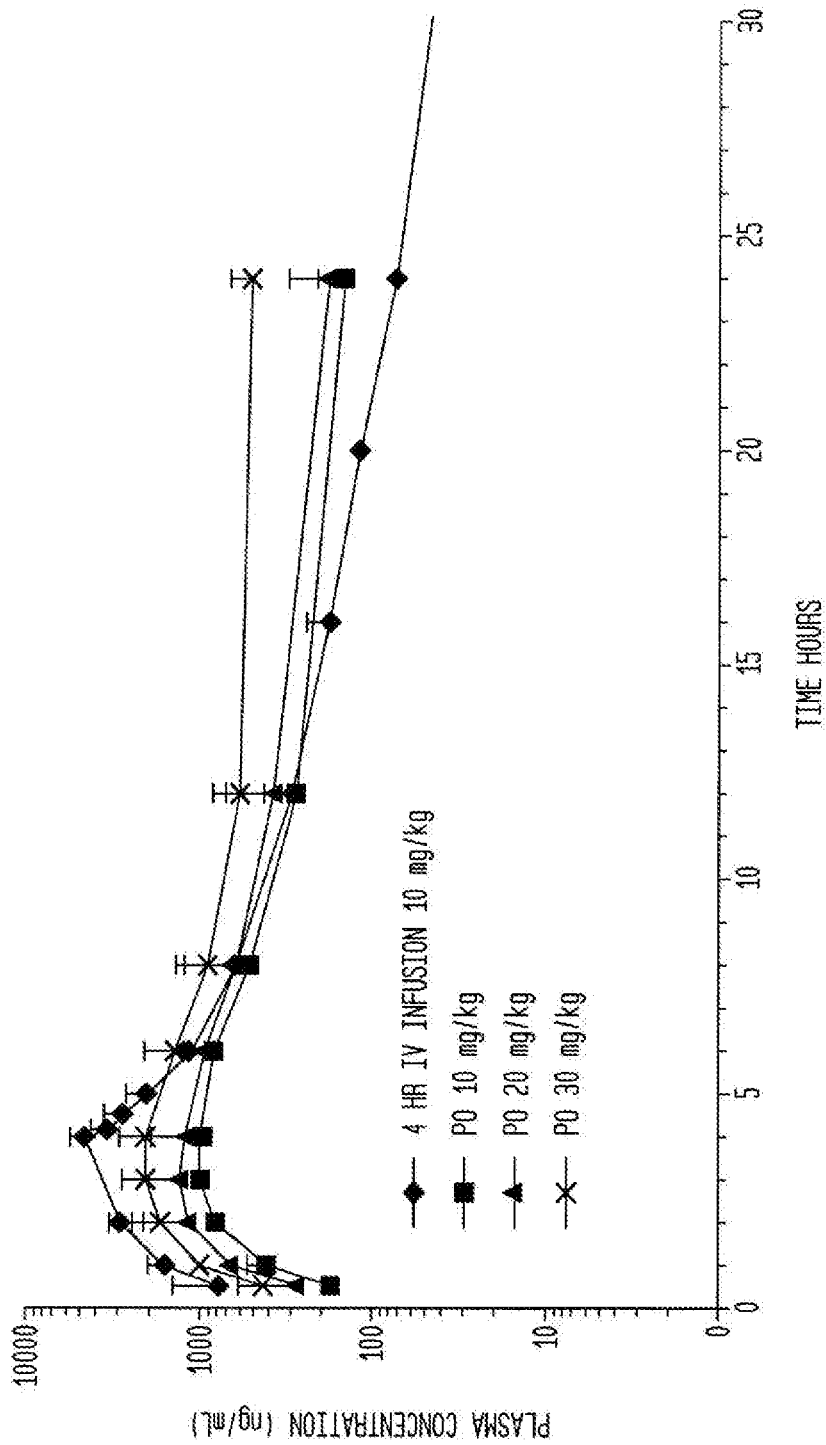
FIG. 11 depicts pharmokinetic profile of intravenous administration of ST-246 as compared to oral administration of ST-246.
Figure 12:
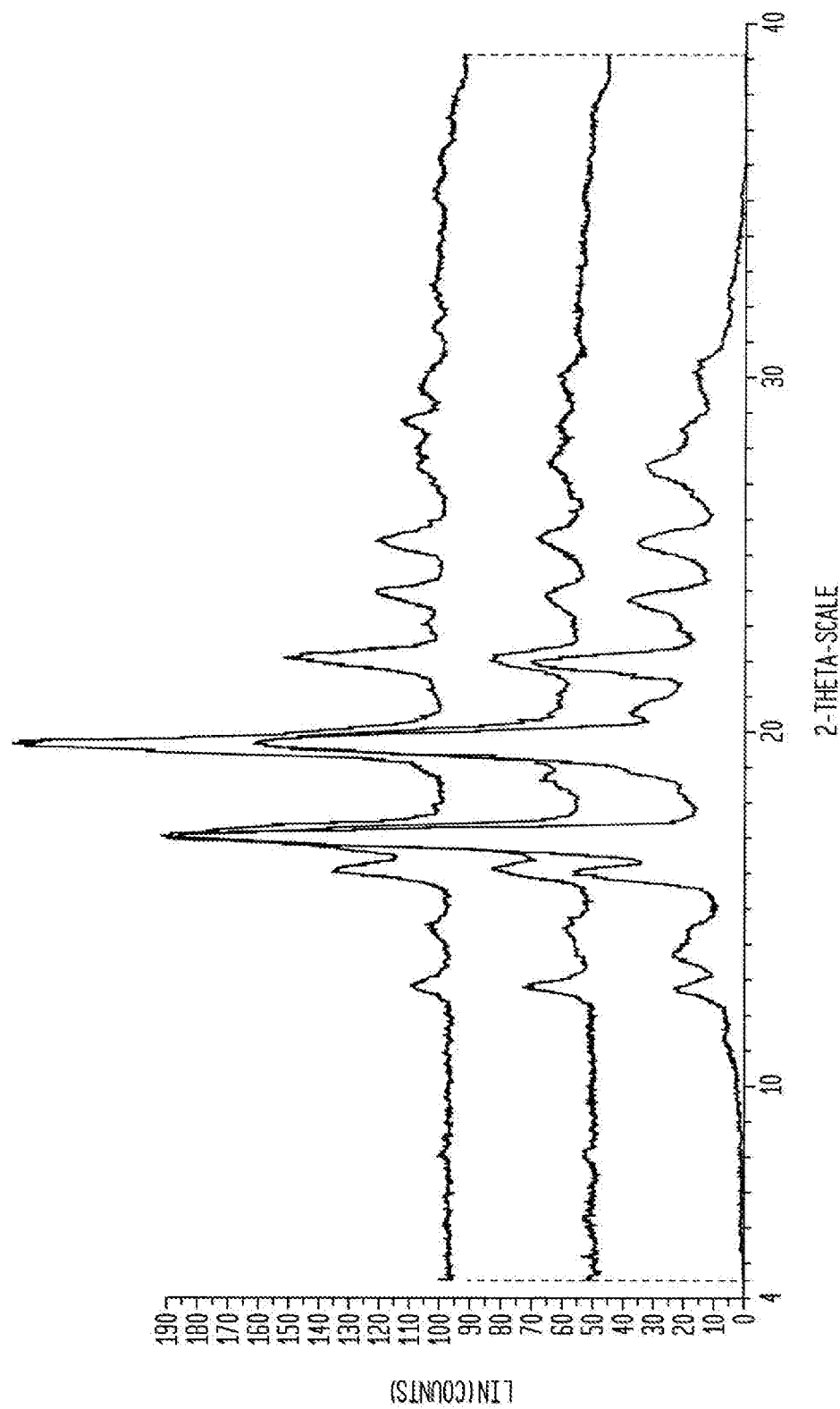
FIG. 12 shows three X-ray powder diffraction (XRPD) patterns of Form II (from three different samples).

Further, as shown in FIG. 11, The ST-246 IV and the oral formulations show comparable pharmacokinetic profile. Furthermore these results suggest that the IV route of ST-246 administration can provide stable and predictable pharmacokinetics over the potential therapeutic dose range.

Example 4—Comparison of the Safety and Pharmacokinetics of ST-246 After IV Infusion or Oral Administration in Mice, Rabbits and Monkeys A liquid formulation has been developed for IV administration of ST-246 containing hydroxoy-propyl beta cyclodextrin in aqueous solution. The tolerability and pharmacokinetics of this formulation have been evaluated in mice, rabbits and NHP in order to determine the optimal administration strategy. The results are compared with the pharmacokinetics observed after oral administration.

Study Designs and Animal In-Life Studies

Oral Studies

ST-246 was administered by oral gavage as a methylcellulose suspension formulation with 1% Tween 80 to BALB/c mice (Charles River), New Zealand White (NZW) rabbits (Harlan), and cynomolgus monkeys (NHP, Charles River). NHP were administered ST-246 immediately after feeding to increase the bioavailability (6). Female BALB/c mice were administered the suspension formulation via oral gavage at doses of 30, 100, 300, and 1000 mg/kg. Concentrations of ST-246 were measured by taking blood samples from three mice at each of the following time points: 0.5, 1, 2, 3, 4, 5, 6, 8, 10, 12, and 24 hours post dose. Three male and three female NZW rabbits were administered ST-246 orally as a suspension formulation at a dose of 100 mg/kg. Blood was collected at the following time points for determination of ST-246 concentration: 0.5, 1, 2, 3, 4, 5, 6, 8, 12, and 24 hours after administration. Three male and three female NHP per dose group were administered the following oral doses of ST-246 in the fed state: 0.3, 3, 10, 20, and 30 mg/kg. Blood samples were collected predose and at 0.5, 1, 2, 3, 4, 6, 8, 12, and 24 hours after dose administration to measure ST-246 concentration.

IV Infusion Studies

The pharmacokinetics and tolerability of a solution formulation of ST-246 administered by IV infusion were evaluated in three animal species: female BALB/c (Charles River) and CD-1 mice (Charles River), NZW rabbits (Harlan), and cynomolgus monkeys (Charles River).

A slow push (5 minute) IV injection of a solution formulation of ST-246 was administered to a small number of catheterized female BALB/c mice at doses of 3, 30, and 100 mg/kg. Blood samples were collected at 5, 15, 30 minutes and 1, 2, 4, 8, and 24 hours after IV administration for the 10 and 30 mg/kg dose, but only at 2 and 4 hours after dose administration for the 100 mg/kg dose. Patency difficulties in the catheters limited the number of mice per time point to no more than two. A 10-minute IV infusion of ST-246 was given via a surgically implanted jugular cannula at doses of 3, 10, 30, and 75 mg/kg to catheterized naïve female CD-1 mice. Blood samples were collected at 5, 10 (end of infusion), 20, 30 minutes, and 1, 2, 4, 8, 24 hours post dose. Blood samples for each time point were collected from three animals as terminal bleeds.

In rabbits, ST-246 was infused via the marginal ear vein at doses of 3, 30, and 60 mg/kg over a 5-minute period and at 3 mg/kg over a 15-minute period followed by blood sampling at multiple times in order to generate complete plasma concentration time curves. Two male and two female rabbits were used for each dose group. For the 5-minute slow push IV injection, blood samples were collected at 10 minutes (5 minutes after the end of the injection), 20 and 30 min, 1, 2, 4, 8, and 24 hours after administration. Blood samples for the 15-minute IV infusion were taken at the end of the infusion (15 minutes), 25 and 45 minutes, and 1, 2, 4, 8, and 24 hours after the beginning of the infusion.

Nonhuman primates (NHP) were prepared for ST-246 administration by surgical implantation of a catheter in the femoral vein that was routed to a subcutaneous port. Doses of 1, 3, 10, 20, and 30 mg/kg were infused over 4 hours to groups consisting of two male and two female NHP. Two additional groups were administered the 20 and 30 mg/kg doses over 6 hours. For the 4 hour IV infusion group, blood was collected for ST-246 analysis at the following time points: 0.5, 1, 2, 4 (end of infusion), 4.25, 4.5, 5, 6, 8, 12, 16, 20, 24, and 48 hours after the start of the infusion. For the 6-hour IV infusion, the samples were collected at the following time points: 1, 2, 4, 6 (end of infusion), 6.25, 6.5, 8, 10, 12, 16, 20, 24, and 48 hours after initiation of dose administration. Blood samples were collected at multiple time points to allow complete characterization of the plasma concentration time curve and estimate the pharmacokinetic parameters. Two groups of 4 males and 4 females were used in a second study that was conducted after a 10 day washout. In the second phase, the pharmacokinetic parameters were characterized over the course of a twice daily (BID) regimen for doses of 10 and 15 mg/kg that were infused over two 4 hour infusion periods initiated 12 hours apart. The total daily doses were 20 and 30 mg/kg, equivalent to the two highest doses that had been evaluated during both 4 and 6 hour IV infusions. For the BID study, blood was collected at the following time points for ST-246 concentration determination: 0.5, 2, 4 (end of first infusion), 4.5, 6, 8, 12, 12.5, 14, 16 (end of second infusion), 16.5, 18, 20, 24, 32, 36 and 60 hours after the beginning of infusion of the first dose.

Tolerability and Toxicological Evaluation

Cage-side observations were made throughout all of these studies for general appearance, behavior, mortality and moribundity. Preclinical evaluations for adverse events (AEs) such as vital sign measurements, physical examinations, and neurologic exams were assessed throughout the studies in NHP.

Bioanalytical Methods

ST-246 concentrations in mice, rabbit and NHP plasma were measured using a liquid chromatography-tandem mass spectrometry (LC-MS/MS) method. Blank plasma for calibration curves and quality control samples were purchased from Bioreclamation, Inc. (Westbury, N.Y.). Two different extraction methods were used over the course of these studies. Both methods were validated following the FDA bioanalytical validation guidelines (7). In one method, the extraction of ST-246 from plasma was carried out by simple protein precipitation by the addition of 9 parts methanol (450 µL) containing the isotopic internal standard to 1 part (50 µL) plasma sample. After high speed centrifugation 100 µL of supernatant was added to 200 µL of compensation solution (0.05% acetic acid in 0.05% ammonium hydroxide: methanol; 36:55, v/v) and directly injected onto the LC-MS.

The second extraction method was a liquid-liquid extraction (LLE) method. Plasma samples were diluted 1:1 with methanol containing internal standard and three volumes of water added. These mixtures were vortexed and the entire volume transferred to the extraction plate (Biotage SLE, 200 mg). Minimal vacuum was applied to load the samples and then allowed to stand for 5 minutes. Methyl tertiary-butyl ether was added to all wells (500 µL/well) and eluted with minimal vacuum. The solvent was evaporated to dryness under nitrogen (set at 50° C. and 30-40 L/min). The samples were reconstituted (0.05% acetic acid and 0.05% ammonium hydroxide in methanol/water; 65:35, v/v) by gently vortexing the plate afterwards.

The chromatographic separation was performed using a Phenyl-Hexyl column (50×2.0 mm, 5 µm, Phenomenex) with a Securityguard column, using 0.05% ammonium hydroxide and 0.05% acetic acid in MeOH/H$_2$O (65:35, v/v) at a flow rate of 400 µL/min for the mobile phase. A 3200 (or 4000) Qtrap (AB Sciex) mass spectrometer was tuned to the multiple reaction monitoring (MRM) mode to monitor the m/z transitions, 375.0/283.2 for ST-246 and m/z 341.1/248.8 for the internal standard, in negative ion mode. The MS/MS response was (1/x$^2$) weighted linearly over the concentration range from 5.00 to 2000 ng/mL. The accuracy and precision of the method were within the acceptable limits of ±20% at the lower limit (5.0 ng/mL) of quantitation and ±15% at other concentrations.

Pharmacokinetic Analysis

Pharmacokinetic parameters were analyzed with WinNonlin Phoenix version 6.1 (Pharsight, Mountain View, Calif.) software initially using noncompartmental analysis, with compartmental analysis conducted later for some of the studies. The following parameters were estimated: terminal elimination half-life ($t_{1/2}$), the area under the curve (AU-C$_{last}$), the area under the curve extrapolated to infinity (AUC$_{0-inf}$), clearance (CL), and the steady state volume of distribution (V$_{ss}$). The peak plasma concentrations (C$_{max}$) and the time to peak plasma concentration (T$_{max}$) were determined graphically from the experimental values.

Statistical Analysis

Untransformed and dose-normalized data for C$_{max}$ and AUC$_{0-inf}$ were analyzed using the JMP8.0 program (SAS Corporation, Cary, N.C.), which is based on the one-way analysis of variance (ANOVA) regression model, in order to evaluate dose linearity and dose proportionality. Gender differences within the same dose group were evaluated using Student's t-test. A value of p<0.05 was considered statistically significant.

Mouse Studies

Preliminary bolus IV injections of ST-246 in BALB/c mice resulted in some dose-related toxicity and mortality at the highest dose of 34 mg/kg. A slower (5-minute push) IV injection resulted in some clinical signs of labored breathing and lethargy at the 100 mg/kg dose, but was well-tolerated at both 3 and 30 mg/kg. These observations suggested that the toxicity was related to the peak plasma concentration and that slower infusions would allow safe administration of higher doses. Further increasing the duration of administration to mice required changing the mouse strain from BALB/c to the slightly larger CD-1 strain, as significant numbers of catheters in BALB/c mice failed to remain patent. After a study confirmed that this change in mouse strains did not result in significant changes in exposure or pharmacokinetics (data not shown), catheterized female CD-1 mice were administered 10-minute IV infusions at doses of 3, 10, 30 and 75 mg/kg. Although mice that received the highest dose, 75 mg/kg, had an unsteady gait after the end of infusion, they recovered within 2-3 hours. All other doses were well-tolerated when administered as 10-minute IV infusions. The correlation between the clinical signs and the end of the infusions suggests, but does not prove, that the high $C_{max}$ concentrations were responsible for the clinical signs in mice after IV administration at higher doses.

Figure 16:
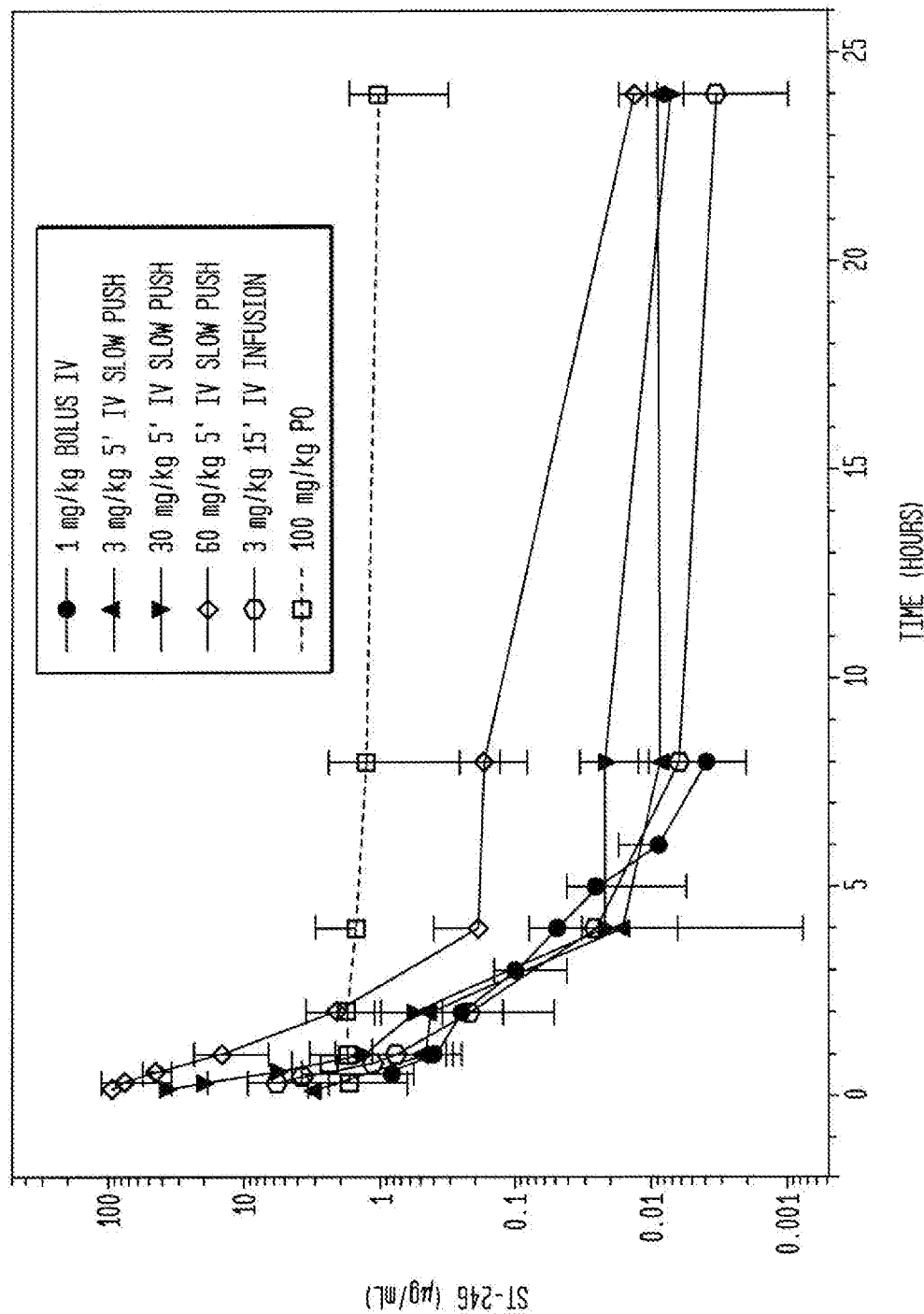
FIG. 16 shows plasma concentration time curves for oral and IV administration of ST-246 in mice. The means and standard deviations of the plasma concentrations over time are shown after oral administration of ST-246 to female BALB/c mice at doses of 30, 100, 300, and 1000 mg/kg. The means and standard deviations of the plasma concentrations over time after 10 minute IV infusions to female CD-1 mice at 3, 10, 30, and 75 mg/kg. Each time point is the mean value from three individual mice.

The results (Table 27 and FIG. 16) show that IV infusion over 10 minutes resulted in very high $C_{max}$ plasma concentrations of ST-246. The mean $C_{max}$ concentration after the 10-minute IV infusion of 75 mg/kg in female CD-1 mice was 238 μg/mL, 3.6-fold higher than the $C_{max}$ observed following a single oral administration of 1000 mg/kg, a 13-fold higher dose, in female BALB/c mice. Although the maximum plasma concentrations after these short IV infusions were much higher than after administration of much higher oral doses (Table 27), the exposure (AUC$_{0-24\ hr}$) was only 1.5-fold higher for the same two dose groups. Comparison of the exposure for the 30 mg/kg oral dose to the 10-minute IV infusion of the same dose showed that ST-246 had approximately 41% bioavailability for that dose. Dose-normalized exposure after oral administration declined with increasing dose, but the same trend was not observed after IV administration.

TABLE 27

Comparison of pharmacokinetic parameters for ST-246 after oral administration to female BALB/c mice and 10-minute IV infusion in female CD-1 mice

| Route | Dose mg/kg | $T_{1/2}$ hr | $C_{max}$ μg/mL | AUC$_{0-24\ hr}$ hr * μg/mL | CL mL/hr/kg |
|---|---|---|---|---|---|
| 10-min IV Infusion | 3 | 4.5 | 17 | 68 | 43 |
|  | 10 | 2.8 | 64 | 408 | 25 |
|  | 30 | 2.5 | 147 | 709 | 42 |
|  | 75 | 2.8 | 238 | 1253 | 60 |
|  |  |  |  |  | CL/F mL/hr/kg |
| PO | 30 | 2.4 | 38 | 292 | 102 |
|  | 100 | 2.2 | 44 | 456 | 219 |
|  | 300 | 4.1 | 64 | 669 | 438 |
|  | 1000 | 4.5 | 66 | 852 | 1133 |

IV, intravenous
PO, per oral

The elimination half-lives were similar for the IV infusion and oral doses, those for the IV infusions doses ranged from 2.5 to 4.5 hours, while those for the oral doses ranged from 2.2 to 4.5 hours. These values were very close to what has been consistently observed throughout the oral nonclinical safety toxicokinetics studies in BALB/c mice. Clearance was relatively consistent after IV infusion over the 3-75 mg/kg dose range, while the apparent clearance after oral dosing increased approximately 10-fold over the approximately 30-fold dose range. FIG. 1 clearly illustrates that even short IV-infusions in mice provided plasma exposure over time similar to that observed after oral administration, albeit with higher maximum plasma concentrations.

Rabbit Studies

The tolerability and pharmacokinetics of IV administration of ST-246 was compared to that of oral administration in NZW rabbits. Although a preliminary study had shown that IV bolus administration of 1 mg/kg was well tolerated, the IV infusion studies results in mice indicated a potential for a lack of tolerability after rapid IV administration of the highest doses. Therefore, ST-246 was administered as 5-minute slow push IV injections at doses of 3, 30, and 60 mg/kg in NZW rabbits via the marginal ear vein. Whereas the 3 and 30 mg/kg doses were well-tolerated, rabbits administered the 60 mg/kg dose exhibited lethargy, labored breathing and narcosis immediately following injection. These animals appeared to recover fully 30-60 minutes after the injections. A slower (15 minute) infusion of the 3 mg/kg dose was also well-tolerated.

The 15-minute IV infusion of 3 mg/kg resulted in a mean $C_{max}$ concentration of 5.79 μg/mL, only two-fold higher than the 2.86 μg/mL observed after oral administration of 100 mg/kg (Table 2). However, the AUC$_{0-24}$ value for the 3 mg/kg IV dose was only 2.38 hr*μg/mL while AUC$_{0-24}$ value for the 100 mg/kg oral dose was 19.8 hr*μg/mL, only 8.3-fold higher exposure for a 33-fold higher dose. Clinical signs in the rabbits were observed only at the 60 mg/kg dose, where the mean $C_{max}$ plasma ST-246 concentration was 94.1 μg/mL, while the mean maximum plasma concentration observed for the well-tolerated 30 mg/kg dose of ST-246 was lower, at 38.5 μg/mL. Whereas the $C_{max}$ values for short IV infusions were much higher than that of a much higher oral dose, 100 mg/kg, the exposures, as determined by the AUC measurements, were much lower. The AUC$_{0-24}$ values observed after the 30 mg/kg dose via intravenous slow push in both genders were comparable to that recorded for the 100 mg/kg oral dosing and notwithstanding the high $C_{max}$; it was evident from the cage side observations that the test article and delivery rate at this dose was well tolerated in rabbits. As was observed with mice, short intravenous infusions in rabbits produced very high maximal ST-246 concentrations, which corresponded with the times of the observed clinical signs in the animals. The AUC values, although higher than corresponding oral dosing, did not correlate with clinical signs observed in these studies. The pharmacokinetic parameters in rabbits were evaluated using a 15-minute IV infusion of 3 mg/kg ST-246. In the 15-minute IV infusion study, blood samples were taken immediately at the end of infusion instead of 5 minutes after the end of infusion as in the initial IV infusion study. The $C_{max}$ from the second study was therefore a more accurate reflection of $C_{max}$ than that of the initial 5-minute IV infusion study and, in fact, the $C_{max}$ values were substantially higher (See Table 2). The results from the single longer infusion confirmed what was observed in the multi-dose study, that the $C_{max}$ values after short IV infusions were much higher than the values observed after equivalent oral doses.

Figure 17:
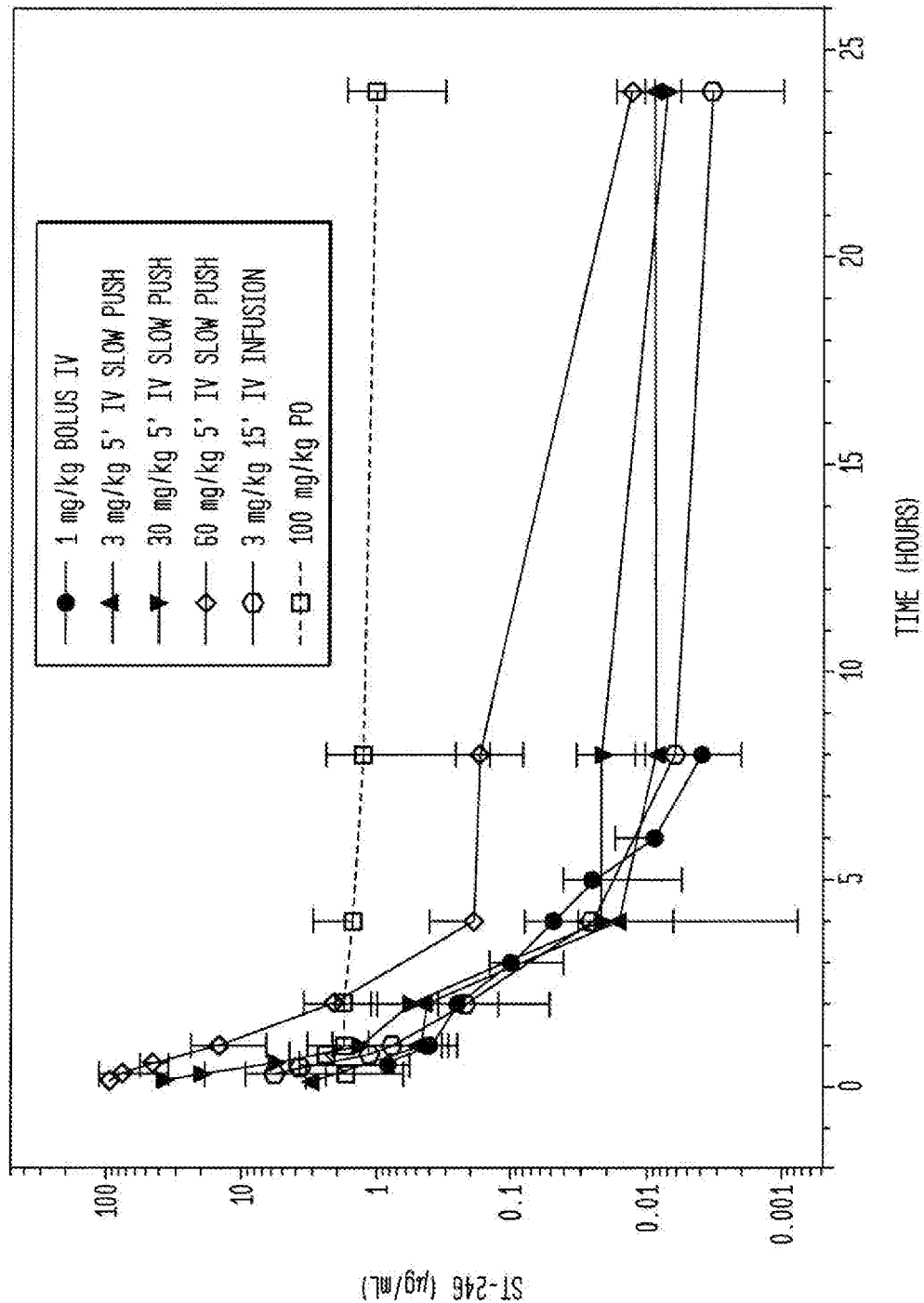
FIG. 17 shows plasma concentrations over time after IV and oral administration in New Zealand White Rabbits. Plasma concentrations of ST-246 over time are shown after oral administration of 100 mg/kg; bolus IV administration of 1 mg/kg; or a 5-minute IV slow push of 3, 30, or 60 mg/kg. A 15-minute IV infusion of 3 mg/kg is also shown. Each curve is the mean with standard deviations from two male and two female rabbits.

The semi-logarithmic graph of the plasma concentration time curves in rabbit IV infusion studies show biphasic distribution and elimination (FIG. 17). There appeared to be an initial rapid distribution phase that was followed by a slower terminal elimination phase. There was no clear dose-related trend in the elimination half-lives after IV infusion in rabbits. The elimination half-lives ranged from approximately 1 hour to 12.2 hours for the IV infusion dose group, while the elimination half-life for the 100 mg/kg oral dose was 3.7 hours (Table 28).

TABLE 28

Comparison of pharmacokinetic parameters for ST-246 after oral administration and IV administration to New Zealand White rabbits.

| Route | Dose mg/kg | $T_{1/2}$ hr | $C_{max}$ µg/mL | $AUC_{0\text{-}24\,hr}$ hr * µg/mL | CL mL/hr/kg |
|---|---|---|---|---|---|
| IV Bolus | 1 | 0.9 ± 0.2 | 1.67 ± 2.27 | 1.43 ± 0.40 | 1660 ± 2166 |
| 15-min IV Infusion | 3 | 1.2 ± 1.1 | 5.79 ± 3.67 | 3.39 ± 1.07 | 966 ± 363 |
| *IV Slow Push (5-min) | 3 | 3.2 ± 0.0 | 3.03 ± 0.37 | 2.38 ± 0.93 | 1339 ± 521 |
| *IV Slow Push (5-min) | 30 | 12.2 ± 5.8 | 38.5 ± 3.7 | 13.3 ± 0.7 | 2229 ± 134 |
| *IV Slow Push (5-min) | 60 | 5.2 ± 0.8 | 94.1 ± 11.1 | 61.8 ± 8.7 | 987 ± 138 |
|  |  |  |  |  | CL/F mL/hr/kg |
| PO | 100 | 3.7 ± 3.2 | 2.86 ± 2.03 | 19.8 ± 16.6 | 7207 ± 6251 |

*Blood draw at taken 5 minutes after actual EOI
EOI, end of infusion
IV, intravenous
PO, per oral NHP Studies ST-246 was administered via IV infusion over 4 hours via surgically implanted vascular access ports in NHP at doses of 1, 3, 10, 20, and 30 mg/kg. The plasma concentrations increased throughout the 4-hour IV infusion of ST-246, reaching maximum concentrations at the end of the infusion (Table 29, FIG. 18). The maximum plasma concentrations ($C_{max}$) were higher after the IV infusions than after oral administration of equivalent doses (Table 29). At higher doses, the differences between the oral and IV $C_{max}$ concentrations increased. The $C_{max}$ concentrations after oral administration increased less than dose-proportionally, while the peak plasma concentrations after IV infusion increased more than would be expected based on dose-proportionality.

TABLE 29

Comparison of pharmacokinetic parameters for ST-246 after oral administration and IV infusions in cynomolgus monkeys.

| Dose (mg/kg) | $T_{1/2}$ (hr) | $T_{max}$ (hr) | $C_{max}$ (µg/mL) | $AUC_{INF\_obs}$ (hr * µg/mL) | CL (mL/hr/kg) |
|---|---|---|---|---|---|
| 4 Hr-IV Infusion | | | | | |
| 1 | 6.6 ± 6.0 | 4 | 0.384 ± 0.112 | 1.94 ± 0.46 | 537 ± 117 |
| 3 | 8.5 ± 3.2 | 4 | 1.05 ± 0.19 | 5.83 ± 0.87 | 523 ± 77 |
| 10 | 8.6 ± 1.3 | 4 | 4.40 ± 0.94 | 21.3 ± 3.4 | 478 ± 71 |
| 4 Hr-IV Infusion | | | | | |
| 20 | 8.7 ± 2.5 | 4 | 11.8 ± 2.0 | 59.6 ± 10.1 | 353 ± 59 |
| 30 | 7.8 ± 0.7 | 4 | 20.1 ± 4.2 | 100 ± 18 | 307 ± 59 |
| 6 Hr-IV Infusion | | | | | |
| 20 | 6.6 ± 2.3 | 6 | 7.48 ± 0.40 | 47.9 ± 6.1 | 433 ± 53 |
| 30 | 6.9 ± 0.8 | 6 | 13.9 ± 1.3 | 87.2 ± 14.6 | 362 ± 61 |
| BID Study 4 Hr IV Infusions SOI 12 Hours Apart Values from First Dose | | | | | |
| 10 | N/A | 4 | 4.59 ± 1.29 | 21.0 ± 5.0 | N/A |
| 15 | N/A | 4 | 7.36 ± 1.47 | 32.5 ± 5.7 | N/A |
| BID Study 4 Hr IV Infusions SOI 12 Hours Apart Values from Second Dose | | | | | |
| 10 | 8.9 ± 2.5 | 4 | 5.18 ± 0.89 | 26.8 ± 5.0 | 429 ± 74 |
| 15 | 9.1 ± 2.6 | 4 | 9.08 ± 0.95 | 48.7 ± 7.5 | 351 ± 44 |
| PO Administration | | | | | |
| 0.3 | 4.0 ± 1.3 | 2.5 | 0.0538 ± 0.0275 | 0.380 ± 0.149 | 920 ± 437 |
| 3 | 9.9 ± 6.0 | 3.3 | 0.496 ± 0.145 | 4.53 ± 0.49 | 669 ± 65 |
| 10 | 7.0 ± 0.9 | 3.8 | 1.08 ± 0.28 | 11.8 ± 3.7 | 918 ± 275 |
| 20 | 7.2 ± 2.3 | 3.2 | 1.71 ± 0.71 | 18.3 ± 7.0 | 12084 ± 385 |
| 30 | 17.7 ± 13.8 | 3.6 | 1.99 ± 0.87 | 31.9 ± 7.4 | 992 ± 281 |

SOI, start of infusion
IV, intravenous
PO, per oral
BID: twice a day

The maximum plasma concentration after oral administration of ST-246 increased only 37-fold as the dose was increased 100-fold, from 0.3 to 30 mg/kg, while the exposure ($AUC_{inf\text{-}obs}$) increased closer to the proportional increase in dose, or 84-fold. The elimination was also biphasic after oral administration, with plasma concentration time curves similar to those observed for rabbits.

Figure 18:
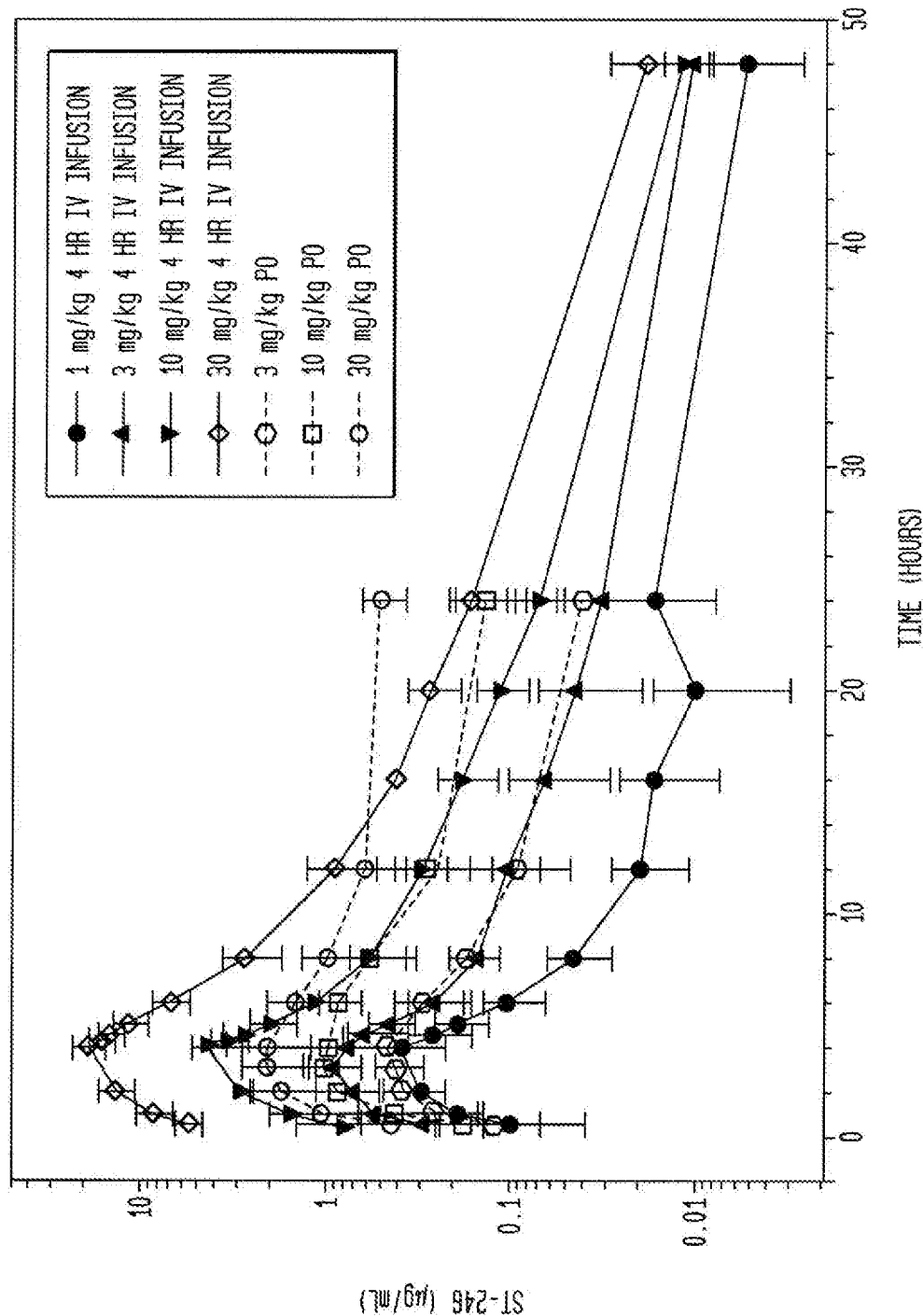
FIG. 18 shows ST-246 plasma concentrations over time after oral administration compared to 4 hour IV infusions in cynomolgus monkeys. Plasma concentration of ST-246 after a single oral dose of 3, 10, or 30 mg/kg compared to the plasma concentration time curves after 4 hour IV infusion of 1, 3, 10, or 30 mg/kg in cynomolgus monkeys. Each curve shows the means and standard deviations. For oral administration there were 3 males and 3 females in each dose group while for the IV infusion there were 2 males and 2 females in each dose group.

The plasma elimination after IV infusion appeared to have at least two distinct phases, with a rapid distribution phase observed at the end of the infusion followed by a much slower terminal elimination phase (FIG. 18). The plasma concentrations fell below the lower limit of quantitation (LLOQ=5.0 ng/mL) before 24 hours for most of the animals in the 1 mg/kg dose group, but ST-246 was above the LLOQ for all other animals in the higher dose groups through the last time point at 48 hours.

The pharmacokinetic (PK) parameters were calculated using noncompartmental analysis for individual animals. For the IV infusions, each dose group consisted of two males and two females, while for the oral dose administration; each dose group had three males and three females. Student's t-test was performed in order to evaluate potential gender differences on the PK parameters of $C_{max}$ and $AUC_{inf}$. There were no statistically significant gender differences (p>0.05) with respect to the $C_{max}$ or $AUC_{inf}$ values at each dose level tested with a 95% confidence interval. Therefore, the mean and standard deviation values were calculated by including all animals from both genders of each dose group. The variability of individual $C_{max}$ or $AUC_{inf}$ values within each dose group was quite small, with the exception of one or two animals that had inadvertent and obvious subcutaneous injections and whose values were excluded from group means.

Figure 19:
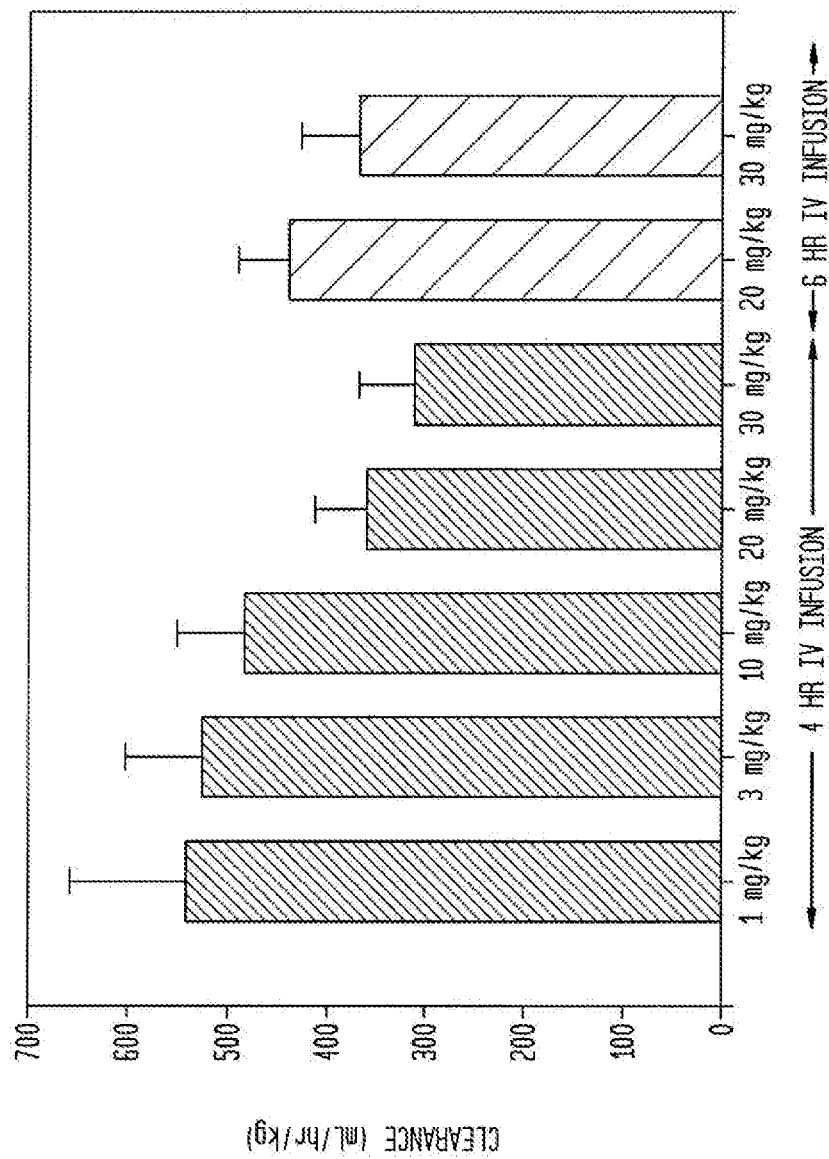
FIG. 19 shows calculated clearance values from IV infusion studies. The means and standard deviations of the calculated clearance for each dose group administered to cynomolgus monkeys as either 4 or 6 hour IV infusions.

Although the $C_{max}$ and $AUC_{inf}$ values increased dose-proportionally as the 4 hour IV-infused doses increased from 1 to 10 mg/kg, the increases in these values were greater than dose-proportional at the 20 and 30 mg/kg doses (Table 29). The $C_{max}$ values for the 3 and 10 mg/kg doses were 2.7-fold and 11.5-fold higher, respectively, than that of the 1 mg/kg dose, while the corresponding values for the 20 and 30 mg/kg doses were 31-fold and 52-fold higher, respectively. The $AUC_{inf}$ values increased 3.0, 11.0, 32, and 53-fold higher for the 3, 10, 20, and 30 mg/kg doses, respectively, compared to the 1 mg/kg dose. The increase in exposure above dose-proportionality was also reflected in the strong trend of decreased clearance (Cl=Dose/AUC) as the dose infused over 4 hours was increased, indicating saturation of either a distribution or elimination mechanism (FIG. 19). Extending the IV infusion length to 6 hours for the 20 and 30 mg/kg doses increased the clearance (and decreased exposure) relative to the shorter infusions. The clearance values for the longer infusions of the higher doses, however, were still lower than the 1, 3, and 10 mg/kg doses. For the 4 hour infusions, the clearance values were not statistically significantly different when evaluated by ANOVA for the dose groups.

The $C_{max}$ plasma concentrations were higher for the 4 hour infusions compared to the 6 hour infusions by approximately 50%, and the exposures calculated for shorter infusions were also higher, although only by approximately 20%. Plasma concentrations after the end of infusions appeared to have at least two phases for all IV infusions, with a rapid distribution phase clearly observed just after the EOI followed by a slower terminal elimination phase. The plasma concentration time curves appeared similar for the two infusion rates and doses, except for the $T_{max}$ and actual plasma concentrations.

The elimination half-lives after IV infusions were relatively constant over the dose range and different lengths of infusions, ranging from 6.6 to 9.1 hours (Table 29). Oral administration of the 30 mg/kg dose resulted in a 17.7 hour terminal elimination half-life, compared to a 9.9 hour half-life for the orally administered 3 mg/kg dose. Oral administration of doses of up to 20 mg/kg had similar elimination half-lives; and these elimination half-lives were very similar to those observed after IV infusions (Table 29).

Figure 20A:
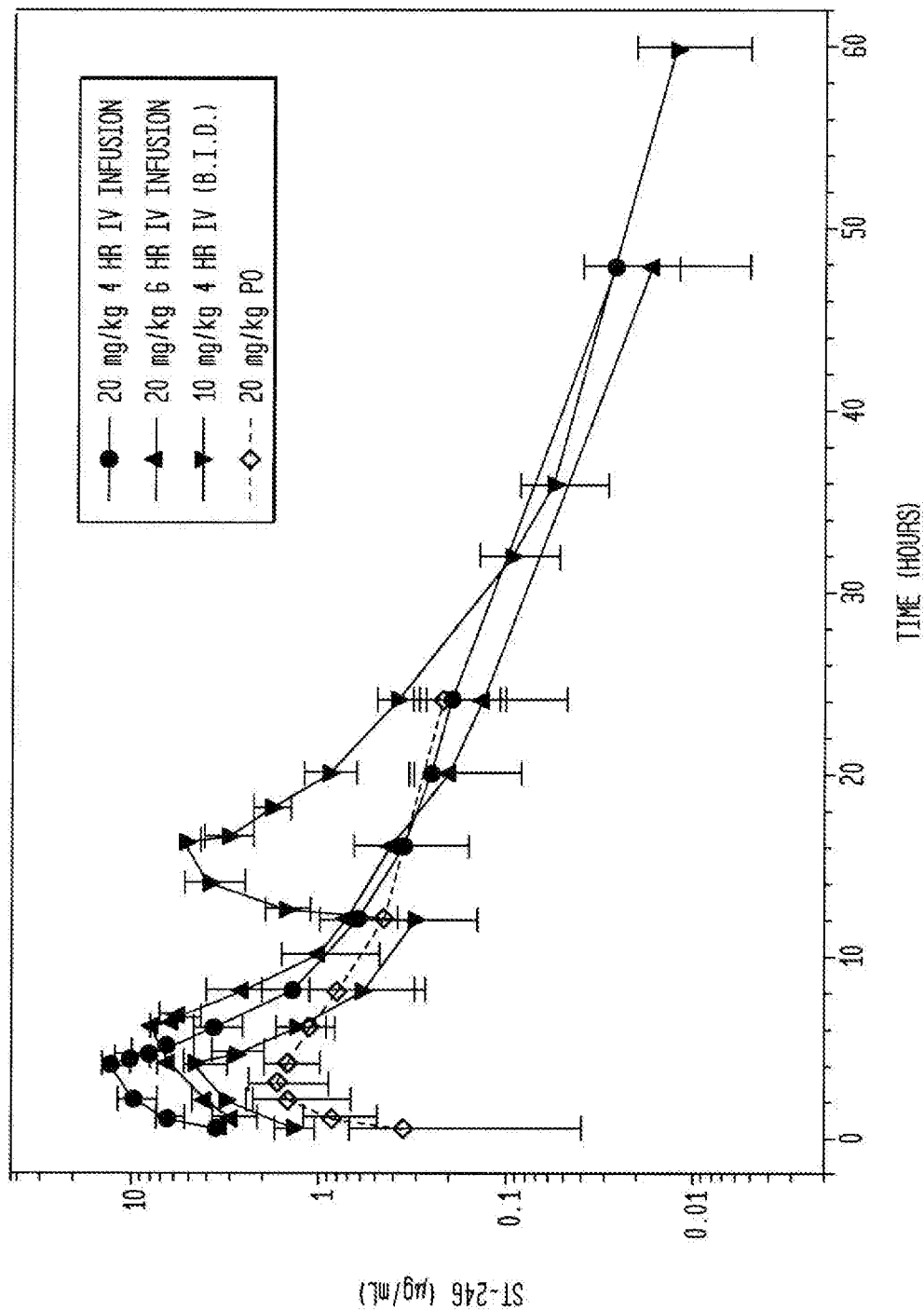
FIGS. 20A and 20B show plasma concentration time curves for different regimens of administration of either 20 or 30 mg/kg ST-246 to cynomolgus monkeys. The mean and standard deviation values for the plasma concentrations over time are shown for different dosing regimens of (FIG. 20A) 20 mg/kg or (FIG. 20B) 30 mg/kg. The dosing regimens included oral administration (3 males and 3 females in each dose group), 4 hour IV infusion (2 males and 2 females in each dose group), 6 hour IV infusion (2 males and 2 females in each dose group), and BID two 4 hour IV infusions initiated 12 hours apart (4 males and 4 females in each dose group).
Figure 20B:
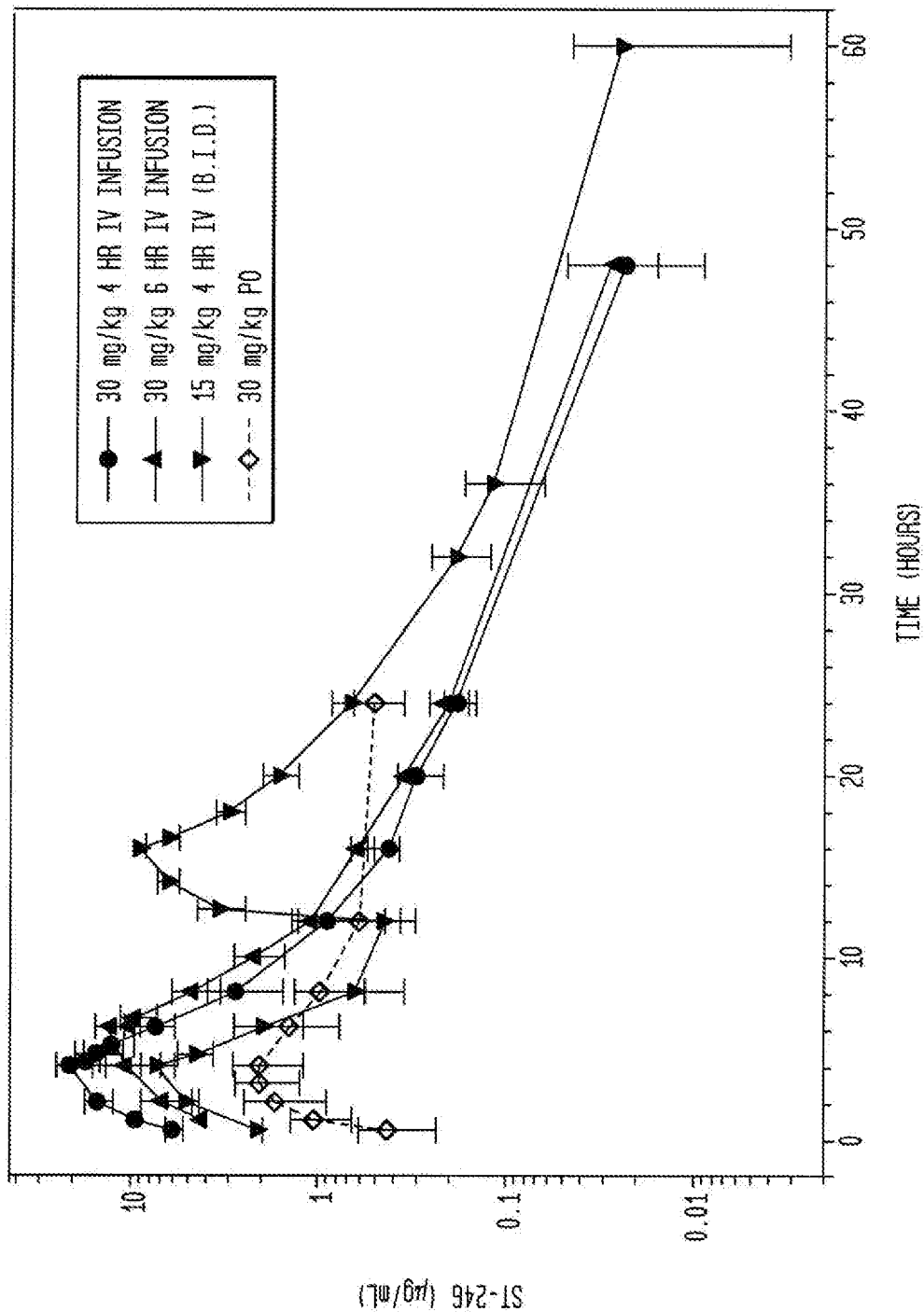

A twice-a-day (BID) administration study of the two highest total daily doses was conducted via two 4 hour IV infusions initiated 12 hours apart over a single 24 hour time period (FIGS. 20A and 20B). The individual doses were 10 and 15 mg/kg, so that the total daily doses were 20 and 30 mg/kg/day for the two dose groups, respectively. Plasma concentrations increased over each of the 4 hour IV infusion periods with the $C_{max}$ for most animals occurring at the end of the infusion. After the end of the first infusion, the plasma ST-246 concentrations decreased until the 12 hour time point, when the second 4 hour IV infusion began. As with the first infusion the plasma concentrations increased until the end of the infusion, and then declined over the remainder of the study. At the last time point, 60 hours after the beginning of the first IV infusion dose, the ST-246 concentration was quite close to the lower limit of quantitation (5 ng/mL) for all of the animals in both dose groups. The semi-logarithmic graphs (FIGS. 20A and 20B) suggest that ST-246 elimination from the plasma after the end of the second infusion was at least biphasic, with a rapid distribution after $T_{max}$ clearly observed, as well as a slower terminal elimination phase for both doses.

The BID administration study had 4 males and 4 females in each dose group, providing a larger number with which to evaluate any potential gender differences in the pharmacokinetic parameters after IV infusion. Student's t-test analysis of the PK parameters ($C_{max}$, $AUC_{last}$ or $AUC_{inf}$, Cl and $V_{ss}$) showed equivalence for the two genders, with the exception of the $C_{max}$ observed during the first phase of dosing at the 10 mg/kg/dose level (p<0.05). Because there were no consistent differences between the pharmacokinetic parameters for the two genders, the final mean and standard deviation values for ST-246 were calculated by combining the data from both genders for each dose group.

The $C_{max}$ and $AUC_{last}$ values for the 15 mg/kg dose were 1.6-fold higher than those of the 10 mg/kg dose during the first 4 hour IV infusion. During the second IV infusion the increase was slightly more, approximately 1.8-fold for the both $C_{max}$ and AUC values. The terminal elimination half-lives, calculated from the second infusion, were essentially identical, 8.9 and 9.1 hours for the two doses, respectively. Clearance was also essentially equivalent for these two doses and within the range observed for the single IV infusions.

As was also observed in the IV infusions studies in mice and rabbits, rapid infusions of the highest doses in NHP, 30 mg/kg infused over 4 hours, resulted in clinical signs, coincident with the end of the infusion. Three out of four animals that received the 30 mg/kg dose of ST-246 over the 4-hour infusion duration exhibited slight generalized tremors. These tremors were observed within 13 minutes of the end of the infusion on the day of dosing and resolved approximately 2 hours after the end of the infusion, indicating reversibility of this toxicity. Tremors were not observed in animals dosed at 30 mg/kg over 6 hours or in any of the animals that received the 20 mg/kg dose via either infusion duration. In addition, no clinical signs were observed throughout the BID study in any of the NHP. The mean peak plasma concentration for the 30 mg/kg 4-hour infusion group was 20.0 µg/mL, while the mean peak plasma concentration for the same dose infused over 6 hours was approximately 13.0 µg/mL. The peak plasma concentrations were much lower in both 20 mg/kg dose groups, as well as the BID study (Table 29).

Discussion

The antiviral efficacy of ST-246 against poxviruses has been demonstrated after oral administration in mice, rabbits, ground squirrels, prairie dogs, and NHP (3, 8-13). The pharmacokinetics of ST-246 after oral administration has been thoroughly characterized in mice, NHP and humans, with limited information in rabbits, rats, and dogs. A complete understanding of the pharmacokinetics is important in species in which the efficacy is also being evaluated, as the selection of the human therapeutic dose will necessarily be chosen based on the animal PK/PD relationship, due to the lack of evaluable orthopox disease in humans. The most relevant animal species for human dose calculation is NHP.

The plasma concentration time curves in rabbits dropped very rapidly after the end of the infusion compared to what had been observed after oral administration, where apparently prolonged absorption provided a long terminal elimination phase with relatively high concentrations after a single oral administration of 100 mg/kg (FIG. 17). Interestingly, as the IV infused dose was increased from 30 to 60 mg/kg, the concentration observed during the terminal elimination phase increased, indicating that higher doses may have, as was observed in NHP, saturated some mechanism of clearance. Additional infusions studies would be needed to confirm the potential relationship between administered dose and clearance in rabbits.

The oral ST-246 study in NHP evaluated the pharmacokinetics over a dose range which encompassed those used in efficacy studies, from 0.3 to 30 mg/kg. The results demonstrated that absorption appeared to be saturated as the orally administered dose was increased, and this was reflected in both the $C_{max}$ concentrations as well as the exposure. Although the $C_{max}$ as well as the exposure increased over this oral dose range, they increased less than dose-proportionally. The $C_{max}$ increased only 37-fold over the 100-fold dose increase, while the exposure, as measured by the $AUC_{inf}$, increased 84-fold, much closer to the 100-fold dose increase.

The saturation of absorption, which led to decreased plasma concentrations and exposure with increasing oral doses, was not observed at similar doses after IV infusions. The bioavailability of ST-246 in NHP based on comparison of identical oral and IV doses ranged from 77% at 3 mg/kg to 31% at 20 and 30 mg/kg doses. After IV infusions, the exposure at these high doses was actually higher than would be expected based on dose-proportional exposure. The exposure for the 4 hour IV infusions of 20 and 30 mg/kg were 30-fold and 50-fold higher, respectively, than the exposure observed after the 1 mg/kg IV infused dose (Table 29). Longer infusions reduced the $C_{max}$ values closer to dose-proportional for the 20 and 30 mg/kg doses, while the AUC values decreased to 25-fold and 45-fold higher than the exposure observed for the 4 hour 1 mg/kg IV infusion (Table 29). The BID dose regimen confirmed the observation that slower infusions decreased not only the $C_{max}$, but reduced the total exposure values to close to dose proportional. These results suggest that a rapid rate of infusion of ST-246 saturated some clearance mechanism. Over a similar dose range, oral absorption may have decreased with increasing dose, so that clearance remained relatively constant, or even increased slightly.

Visual inspection of plasma concentration time curves after oral administration of ST-246 indicates that absorption was prolonged and may have some impact on the apparent elimination half-lives. However, the elimination half-lives did not change significantly for any of the three species studies between oral and IV administration. Given these similar elimination half-lives across all three species examined by oral and IV infusions, it appears that longer IV infusions should be administered in order to reduce the high plasma concentrations, and to avoid the coinciding toxicity, while continuing the once daily dosing regimen that is currently being used in oral studies.

REFERENCES

1. Fenner et al., The epidemiology of smallpox. In: Smallpox and its eradication. Switzerland: World Health Organization; 1988)
2. Bray et al., *Antiviral Research* 58: 101-114 (2003).
3. Quenelle et al. 2007. Efficacy of delayed treatment with ST-246 given orally against systemic orthopoxvirus infections in mice. Antimicrobial Agents and Chemotherapy February; 51(2):689-95
4. Smee et al. (2002) Antimicrob. Agents Chemother. 46:1329-1335)
5. Vora et al., 2008, Severe eczema vaccinatum in a household contact of a smallpox vaccine. Clinical Infectious Disease 15; 46(10):1555-61).
6. Jordan R, Tien D, Bolken T C, Jones K F, Tyavanagimatt S R, Strasser J, Frimm A, Corrado M L, Strome P G, Hruby D E. (2008) Single-dose safety and pharmacokinetics of ST-246, a novel orthopoxvirus egress inhibitor. *Antimicrob Agents Chemother.* 52(5): 1721-7.
7. Guidance for Industry, Bioanalytical Method Validation, U.S. Department of Health and Human Services, Food and Drug Administration, May 2001.
8. Yang G, Pevear D C, Davies M H, Collett M S, Bailey T, Rippen S, Barone L, Burns C, Rhodes G, Tohan S, Huggins J W, Baker R O, Buller R L, Touchette E, Waller K, Schriewer J, Neyts J, DeClercq E, Jones K, Hruby D, Jordan R. (2005) An orally bioavailable antipoxvirus compound (ST-246) inhibits extracellular virus formation and protects mice from lethal orthopoxvirus Challenge. *J Virol.* 79(20): 13139-49.
9. Sbrana E, Jordan R, Hruby D E, Mateo R I, Xiao S Y, Siirin M, Newman P C, D A Rosa A P, Tesh R B. (2007) Efficacy of the antipoxvirus compound ST-246 for treatment of severe orthopoxvirus infection." *Am. J. Trop. Med. Hyg.,* 76(4): 768-773.
10. Nalca A, Hatkin J M, Garza N L, Nichols D K, Norris S W, Hruby D E, Jordan R. (2008) Evaluation of orally delivered ST-246 as postexposure prophylactic and antiviral therapeutic in an aerosolized rabbitpox rabbit model." *Antiviral Res.* 79 (2): 121-7.
11. Huggins J, Goff A, Hensley L, Mucker E, Shamblin J, Wlazlowski C, Johnson W, Chapman J, Larsen T, Twenhafel N, Karem K, Damon I K, Byrd C M, Bolken T C, Jordan R, Hruby D. (2009) Nonhuman primates are protected from smallpox virus or monkeypox virus challenges by the antiviral drug ST-246. *Antimicrob Agents Chemother.* 53 (6): 2620-5.
12. Jordan R, Goff A, Frimm A, Corrado M L, Hensley L E, Byrd C M, Mucker E, Shamblin J, Bolken T C, Wlazlowski C, Johnson W, Chapman J, Twenhafel N, Tyavanagimatt S, Amantana A, Chinsangaram J, Hruby D E, Huggins J. (2009) ST-246 antiviral efficacy in a nonhuman primate monkeypox model: determination of the minimal effective dose and human dose justification. *Antimicrob Agents Chemother.* 53 (5): 1817-22.

13. Robert Jordan, Janet M. Leeds, Shanthakumar Tyavanagimatt and Dennis E. Hruby. (2010) Development of ST-246® for Treatment of Poxvirus Infections. *Viruses* 2: 2409-2435.

The invention claimed is:

1. A unit dosage liquid formulation comprising:
   a) ST-246 content ranging from about 2 mg/ml to about 20 mg/ml; and
   b) hydroxypropyl-β-cyclodextrin content ranging from about 125 mg/ml to about 400 mg/ml.

2. The unit dosage liquid formulation of claim 1 further comprising one or more pharmaceutically acceptable ingredients selected from the group consisting of: mannitol, trehalose dehydrate, lactose monohydrate, and purified water.

3. The unit dosage liquid formulation of claim 1 having a pH range from about 3.0 to about 10.0.

4. The unit dosage liquid formulation of claim 1 having a total volume of about 100 ml.

5. A unit dosage liquid formulation comprising:
   a) ST-246 ranging from about 2 mg/ml to about 20 mg/ml; and
   hydroxypropyl-β-cyclodextrin content ranging from about 12.5 mg/ml to about 40 mg/ml.

6. The unit dosage liquid formulation of claim 5 further comprising one or more pharmaceutically acceptable ingredients selected from the group consisting of:
   polyethylene glycol 400, polysorbate 80, polyethylene glycol 300, and purified water.

7. The unit dosage liquid formulation of claim 5 having a total volume of about 100 ml.

8. The unit dosage liquid formulation of claim 5 having a pH range from about 3.0 to about 10.0.

* * * * *